(12) United States Patent
Vukelic et al.

(10) Patent No.: US 11,559,433 B2
(45) Date of Patent: *Jan. 24, 2023

(54) LASER INDUCED COLLAGEN CROSSLINKING IN TISSUE

(71) Applicant: The Trustees of Columbia University in the City of New York, New York, NY (US)

(72) Inventors: Sinisa Vukelic, New York, NY (US); Gerard A. Ateshian, New York, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 153 days.

This patent is subject to a terminal disclaimer.

(21) Appl. No.: 17/183,041

(22) Filed: Feb. 23, 2021

(65) Prior Publication Data
US 2021/0196509 A1 Jul. 1, 2021

Related U.S. Application Data

(63) Continuation of application No. 15/893,264, filed as application No. PCT/US2016/058353 on Oct. 23, 2016, now Pat. No. 10,940,042.

(Continued)

(51) Int. Cl.
*A61F 9/008* (2006.01)
*A61N 1/44* (2006.01)
(Continued)

(52) U.S. Cl.
CPC ............ *A61F 9/008* (2013.01); *A61B 18/042* (2013.01); *A61B 18/203* (2013.01); *A61B 18/26* (2013.01);
(Continued)

(58) Field of Classification Search
CPC ............ A61F 9/008; A61F 2009/00851; A61F 2009/00872; A61F 2009/00882;
(Continued)

(56) References Cited

U.S. PATENT DOCUMENTS 4,638,801 A   1/1987 Daly et al.
4,784,135 A   11/1988 Blum et al.
(Continued)

FOREIGN PATENT DOCUMENTS

DE   102010020194 A1   11/2011
EP      2283344 A1      2/2011
(Continued)

OTHER PUBLICATIONS

Wang, C., et al. "Femtosecond laser irradiation as novel paradigm for treatment of early osteoarthritis." Annual Meeting of the Orthopaedic Research Society. San Diego, CA, USA. 2017. (Year: 2017).*

(Continued)

*Primary Examiner* — Jonathan T Kuo
(74) *Attorney, Agent, or Firm* — Potomac Law Group, PLLC

(57) ABSTRACT

The presently disclosed subject matter provides techniques for inducing collagen cross-linking in human tissue, such as cartilage, by inducing ionization of the water contained in the tissue to produce free radicals that induce chemical cross-linking in the human tissue. In an embodiment, a femtosecond laser operates at sufficiently low laser pulse energy to avoid optical breakdown of the tissue being treated. In an embodiment, the femtosecond laser operates in the infrared frequency range.

20 Claims, 24 Drawing Sheets

Related U.S. Application Data

(60) Provisional application No. 62/380,713, filed on Aug. 29, 2016, provisional application No. 62/358,035, filed on Jul. 3, 2016, provisional application No. 62/245,805, filed on Oct. 23, 2015.

(51) Int. Cl.
*A61B 18/20* (2006.01)
*A61B 18/26* (2006.01)
*A61B 90/00* (2016.01)
*A61B 18/04* (2006.01)
*A61N 5/06* (2006.01)
*A61B 18/00* (2006.01)
*A61N 5/067* (2006.01)

(52) U.S. Cl.
CPC .............. *A61B 90/361* (2016.02); *A61N 1/44* (2013.01); *A61N 5/062* (2013.01); *A61B 2018/00702* (2013.01); *A61B 2018/00785* (2013.01); *A61B 2018/00791* (2013.01); *A61B 2018/20359* (2017.05); *A61B 2018/20553* (2017.05); *A61B 2018/205545* (2017.05); *A61B 2018/263* (2013.01); *A61F 2009/00851* (2013.01); *A61F 2009/00872* (2013.01); *A61F 2009/00882* (2013.01); *A61F 2009/00897* (2013.01); *A61N 5/067* (2021.08)

(58) Field of Classification Search
CPC ......... A61F 2009/00897; A61B 18/042; A61B 18/203; A61B 18/26; A61B 90/361; A61B 2018/00702; A61B 2018/00785; A61B 2018/00791; A61B 2018/20359; A61B 2018/20553; A61B 2018/205545; A61B 2018/263; A61B 18/20–18/28; A61N 1/44; A61N 5/062; A61N 5/067; A61N 5/06–2005/073
See application file for complete search history.

(56) References Cited

U.S. PATENT DOCUMENTS

| | | | |
|---|---|---|---|
| 4,840,175 A | 6/1989 | Peyman |
| 5,334,190 A | 8/1994 | Seiler |
| 5,556,406 A | 9/1996 | Gordon et al. |
| 5,720,894 A | 2/1998 | Neev et al. |
| 5,735,843 A | 4/1998 | Trokel |
| 5,861,955 A | 1/1999 | Gordon |
| 6,099,521 A | 8/2000 | Shadduck |
| 6,110,166 A | 8/2000 | Juhasz |
| 6,146,375 A | 11/2000 | Juhasz et al. |
| 6,161,546 A | 12/2000 | Yavitz |
| 6,511,800 B1 | 1/2003 | Singh |
| 6,648,877 B1 | 11/2003 | Juhasz et al. |
| 6,902,561 B2 | 6/2005 | Kurtz et al. |
| 6,934,576 B2 | 8/2005 | Camacho et al. |
| 7,241,461 B2 | 7/2007 | Myhill et al. |
| 7,413,781 B2 | 8/2008 | Hubbell et al. |
| 7,645,449 B2 | 1/2010 | Stassi et al. |
| 7,729,749 B2 | 6/2010 | Roessler et al. |
| 8,088,124 B2 | 1/2012 | Loesel et al. |
| 8,114,067 B1 | 2/2012 | Ketteridge et al. |
| 8,215,314 B2 | 7/2012 | Chan et al. |
| 8,262,646 B2 | 9/2012 | Frey et al. |
| 8,279,901 B2 | 10/2012 | Karavitis |
| 8,343,142 B2 | 1/2013 | König et al. |
| 8,366,689 B2 | 2/2013 | Marshall et al. |
| 8,409,177 B1 | 4/2013 | Lai |
| 8,523,846 B2 | 9/2013 | Makino |
| 8,528,566 B2 | 9/2013 | Loesel et al. |
| 8,536,207 B2 | 9/2013 | Koshida et al. |
| 8,545,487 B2 | 10/2013 | Muller et al. |
| 8,569,367 B2 | 10/2013 | Vehige et al. |
| 8,585,686 B2 | 11/2013 | Bergt et al. |
| 8,617,147 B2 | 12/2013 | Knox et al. |
| 8,688,199 B2 | 4/2014 | Dudhia et al. |
| 8,784,406 B2 | 7/2014 | Rathjen |
| 8,915,905 B2 | 12/2014 | Vogler et al. |
| 8,974,444 B2 | 3/2015 | Alfano et al. |
| 9,095,414 B2 | 8/2015 | Jester et al. |
| 9,101,446 B2 | 8/2015 | Bor et al. |
| 9,125,599 B2 | 9/2015 | Chen |
| 9,125,856 B1 | 9/2015 | Paik et al. |
| 9,155,652 B2 | 10/2015 | Peyman |
| 9,226,853 B2 | 1/2016 | Bor et al. |
| 9,271,870 B2 | 3/2016 | Palanker et al. |
| 9,504,607 B2 | 11/2016 | Russmann |
| 9,539,143 B2 | 1/2017 | Holliday et al. |
| 9,545,340 B1 | 1/2017 | Knox et al. |
| 9,555,111 B2 | 1/2017 | Rubinfeld et al. |
| 9,622,911 B2 | 4/2017 | Rubinfeld et al. |
| 9,622,912 B2 | 4/2017 | Knox et al. |
| 9,681,984 B2 | 6/2017 | Peyman |
| 9,695,218 B2 | 7/2017 | Yang et al. |
| 9,814,567 B2 | 11/2017 | Peyman |
| 9,883,970 B2 | 2/2018 | Lopath et al. |
| 10,448,819 B2 | 10/2019 | Weeber |
| 10,940,042 B2 * | 3/2021 | Vukelic .................. A61B 18/26 |
| 2005/0119587 A1 | 6/2005 | Roessler et al. |
| 2005/0129685 A1 | 6/2005 | Cao et al. |
| 2007/0049808 A1 | 3/2007 | Roessler et al. |
| 2007/0213792 A1 | 9/2007 | Yaroslavsky et al. |
| 2008/0031923 A1 | 2/2008 | Murray et al. |
| 2008/0094572 A1 | 4/2008 | Lai |
| 2009/0024117 A1 | 1/2009 | Muller |
| 2009/0171325 A1 | 7/2009 | Koenig |
| 2009/0171327 A1 | 7/2009 | Kurtz et al. |
| 2010/0004643 A1 | 1/2010 | Frey et al. |
| 2010/0027282 A1 | 2/2010 | Gebauer et al. |
| 2010/0210996 A1 | 8/2010 | Peyman |
| 2010/0216226 A1 | 8/2010 | Hyde et al. |
| 2010/0272824 A1 | 10/2010 | Lupton et al. |
| 2010/0286156 A1 | 11/2010 | Pinelli |
| 2010/0318017 A1 | 12/2010 | Lewis et al. |
| 2011/0077624 A1 | 3/2011 | Brady et al. |
| 2011/0208300 A1 | 8/2011 | de Juan et al. |
| 2012/0078240 A1 | 3/2012 | Spooner |
| 2012/0083772 A1 | 4/2012 | Rubinfeld et al. |
| 2012/0083776 A1 | 4/2012 | Dai et al. |
| 2012/0310223 A1 | 12/2012 | Knox et al. |
| 2012/0330291 A1 | 12/2012 | Jester et al. |
| 2013/0110091 A1 | 5/2013 | Berry |
| 2013/0116757 A1 | 5/2013 | Russmann |
| 2013/0245536 A1 | 9/2013 | Friedman et al. |
| 2013/0245617 A1 | 9/2013 | Rathjen |
| 2013/0267528 A1 | 10/2013 | Pinelli |
| 2013/0338650 A1 | 12/2013 | Jester et al. |
| 2014/0066835 A1 | 3/2014 | Muller et al. |
| 2014/0114296 A1 | 4/2014 | Woodley et al. |
| 2014/0155871 A1 | 6/2014 | Cumming |
| 2014/0155872 A1 | 6/2014 | Stevens |
| 2014/0171927 A1 | 6/2014 | Depfenhart |
| 2014/0275935 A1 | 9/2014 | Walsh et al. |
| 2015/0032091 A1 | 1/2015 | Teuma et al. |
| 2015/0126921 A1 | 5/2015 | Rubinfeld et al. |
| 2015/0133901 A1 | 5/2015 | Serdarevic et al. |
| 2015/0144792 A1 | 5/2015 | Gunn |
| 2015/0202085 A1 | 7/2015 | Lemonis et al. |
| 2015/0305933 A1 | 10/2015 | Zhou |
| 2015/0359668 A1 | 12/2015 | Kornfield et al. |
| 2016/0059032 A1 | 3/2016 | Skerl |
| 2016/0081852 A1 | 3/2016 | Peyman |
| 2016/0101045 A1 | 4/2016 | Raymond et al. |
| 2016/0106590 A1 | 4/2016 | Bischoff et al. |
| 2016/0136109 A1 | 5/2016 | Isenburg et al. |
| 2016/0151202 A1 | 6/2016 | Scarcelli et al. |
| 2016/0302971 A1 | 10/2016 | Morley et al. |
| 2016/0310319 A1 | 10/2016 | Friedman et al. |
| 2016/0338588 A1 | 11/2016 | Friedman |
| 2016/0374857 A1 | 12/2016 | Fu et al. |
| 2016/0374858 A1 | 12/2016 | Goos et al. |
| 2017/0021021 A1 | 1/2017 | Kamaev et al. |

(56) References Cited

U.S. PATENT DOCUMENTS

| | | |
|---|---|---|
| 2017/0043015 A1 | 2/2017 | Alageel et al. |
| 2017/0246471 A1 | 8/2017 | Lopath |
| 2017/0319383 A1 | 11/2017 | Luttrull et al. |
| 2018/0021086 A1 | 1/2018 | Deladurantaye et al. |
| 2018/0021172 A1 | 1/2018 | Zheleznyak et al. |
| 2018/0050104 A1 | 2/2018 | Xie et al. |
| 2018/0160898 A1 | 6/2018 | Yoo et al. |
| 2018/0177550 A1 | 6/2018 | Anderson et al. |
| 2018/0221201 A1 | 8/2018 | Vukelic et al. |
| 2021/0187165 A1* | 6/2021 | Vukelic ............... A61L 27/3687 |

FOREIGN PATENT DOCUMENTS

| | | |
|---|---|---|
| EP | 1742311 B1 | 3/2011 |
| EP | 2872082 B1 | 9/2020 |
| WO | 1998005279 A1 | 2/1998 |
| WO | 2000074648 A2 | 12/2000 |
| WO | 2006061565 A1 | 6/2006 |
| WO | 2009073600 A1 | 6/2009 |
| WO | 2011046236 A9 | 7/2011 |
| WO | 2012145159 A1 | 10/2012 |
| WO | 2014065863 A1 | 5/2014 |
| WO | 2014159691 A1 | 10/2014 |
| WO | 2014210152 A2 | 12/2014 |
| WO | 2015010119 A2 | 1/2015 |
| WO | 2015138786 A1 | 9/2015 |
| WO | 2015162559 A1 | 10/2015 |
| WO | 2015138794 A9 | 3/2016 |
| WO | 2016100411 A2 | 6/2016 |
| WO | 2017031167 A1 | 2/2017 |
| WO | 2017070637 A1 | 4/2017 |
| WO | 2018119453 A1 | 6/2018 |

OTHER PUBLICATIONS

Extended European Search Report dated Sep. 27, 2021 for European Patent Application No. 19744571.1.

Albro et al., "Synovial Fluid and Physiologic Levels of Cortisol, Insulin, and Glucose in Media Maintain the Homeostasis of Immature Bovine Cartilage Explants over Long Term Culture"; Annual Meeting of the Orthopedic Research Society, New Orleans, LA, USA, 2013.

Alexandrov et al., "A trust-region framework for managing the use of approximation models in optimization", Structural Optimization, vol. 15, pp. 16-23, Springer-Verlag, 1998.

Alió et al., "Cross-linking in progressive keratoconus using an epithelial debridement or intrastromal pocket technique after previous corneal ring segment implantation", J Refract Surg, 2011, vol. 27, pp. 737-743.

Aristeidou et al., "The evolution of corneal and refractive surgery with the femtosecond laser", Eye Vis (Lond), Jul. 14, 2015, vol. 2(12), pp. epub.

Ashkavand et al., "The pathophysiology of osteoarthritis", Journal of Pharmacy Research, vol. 7(1), pp. 132-138, 2013.

Asri et al., "Corneal collagen crosslinking in progressive keratoconus: Multicenter results from the French National Reference Center for Keratoconus", Journal of Cataract & Refractive Surgery, vol. 37(12), pp. 2137-2143, 2011.

Bakilan et al., "Effects of Native Type II Collagen Treatment on Knee Osteoarthritis: A Randomized Controlled Trial", Eurasian Journal of Medicine, vol. 48(2), pp. 95-101, Jun. 2016.

Bekesi et al., "Biomechanical Changes After In Vivo Collagen Cross-Linking With Rose Bengal-Green Light and Riboflavin-UVA", Invest Ophthalmol Vis Sci, Mar. 1, 2017, vol. 58(3), pp. 1612-1620.

Bi et al., "A novel method for determination of collage orientation in cartilage by Fourier transform infrared imaging spectroscopy (FT-Iris)", Osteoarthritis and Cartilage, vol. 13; pp. 1050-1058, 2005.

Bikbova et al., "Transepithelial corneal collagen cross-linking by iontophoresis of riboflavin", Acta Ophthalmol, 2014, [Epub ahead of print].

Bradford et al., "Custom built nonlinear optical crosslinking (NLO CXL) device capable of producing mechanical stiffening in ex vivo rabbit corneas", Biomedical Optics Express, vol. 8(10), pp. 4788-4797, Sep. 2017.

Caporossi et al., "Long-term Results of Riboflavin Ultraviolet A Corneal Collagen Cross-linking for Keratoconus in Italy: The Siena Eye Cross Study" Am J Ophthalmol. Apr. 2010; 149(4): pp. 585-593.

Caporossi et al., "Riboflavin-UVA-induced corneal collagen cross-linking in pediatric patients", Cornea, 2012, vol. 31, pp. 227-231.

Chai et al., "Nonlinear optical collagen cross-linking and mechanical stiffening: a possible photodynamic therapeutic approach to treating corneal ectasia", Journal of Biomedical Optics, vol. 18(3), 038003-1-038003-8, 2013.

Chai et al., "Quantitative assessment of UVA-riboflavin corneal cross-linking using nonlinear optical microscopy", Investigative Ophthalmology & Visual Science, Jun. 1, 2011, vol. 52(7), pp. 4231-4238.

Chan et al., "Photochemical crosslinking improves the physicochemical properties of collagen scaffolds", Journal of Biomedical Materials Research Part A, Aug. 16, 2005, vol. 75(3), pp. 689-701.

Chen et al., "Corneal biomechanical measurements before and after laser in situ keratomileusis", J Cataract Refract Surg, 2008, vol. 34, pp. 1886-1891.

Chen et al., "IntraLase femtosecond laser vs mechanical microkeratomes in LASIK for myopia: a systematic review and meta-analysis", Journal of Refractive Surgery, vol. 28(1), pp. 15-24, 2012.

Cherfan et al., "Collagen cross-linking using rose bengal and green light to increase corneal stiffness", Invest Ophthalmol Vis Sci, May 13, 2013, vol. 54(5), pp. 3426-3433.

Chu et al., "Early diagnosis to enable early treatment of pre-osteoarthritis"; Arthritis Research & Therapy, Jun. 7, 2012.

Clinical Trial No. NCT02208089, "Simultaneous TransPRK and Corneal Collagen Cross-Linking (TransPRKCXL)", Sponsor: Bruce Allan, Moorfields Eye Hospital NHS Foundation Trust, Aug. 4, 2014.

Collier et al., "Estimated burden of Keratitis—United States, 2010", MMWR Morb Mortal Wkly Rep, vol. 63(45), pp. 1027-1030, Nov. 14, 2014.

Daxer et al., "Corneal crosslinking and visual rehabilitation in keratoconus in one session without epithelial debridement: new technique", Cornea, 2010, vol. 29, pp. 1176-1179.

De Macedo et al., "Femtosecond laser-assisted deep anterior lamellar keratoplasty in phototherapeutic keratectomy versus the big-bubble technique in keratoconus", International Journal Ophthalmology, vol. 11(5), pp. 807-812, May 2018.

De Medeiros et al., "Effect of femtosecond laser energy level on corneal stromal cell death and inflammation", Journal of Refractive Surgery, vol. 25(10), pp. 869-874, Apr. 2009.

De Ortueta et al., "High-speed recording of thermal load during laser trans-epithelial corneal refractive surgery using a 750 Hz ablation system," Journal of Optometry, Jul. 20, 2018, vol. 12 (2), pp. 84-91.

Deberg et al., "New serum biochemical markers (Coll 2-1 and Coll 2-1 NO2) for studying oxidative related type II collagen network degradation in patients with osteoarthritis and rheumatoid arthritis", Osteoarthritis and Cartilage, Mar. 2005, vol. 13(3), pp. 258-265.

Deibel et al., "Ocular inflammation and infection", Emerg Med Clin North A, May 2013, vol. 21(2), pp. 387-397.

Demirok et al., "Corneal sensation after corneal refractive surgery with small incision lenticule extraction", Optometry and Vision Science, Oct. 1, 2013, vol. 90(10), pp. 1040-1047.

Dijkgraaf et al., "Normal cartilage structure, biochemistry, and metabolism: A review of the literature", J Oral Maxillofac Surg, Oct. 1995; vol. 53(10), pp. 924-929.

Dijkgraaf et al., "The structure, biochemistry, and metabolism of osteoarthritic cartilage: A review of the literature", J Oral Maxillofac Surg, Oct. 1995, vol. 53(10), pp. 1182-1192.

Dinarello, "Interleukin-1", Cytokine & Growth Factor Reviews, vol. 8(4), pp. 253-265, 1997.

(56) References Cited

OTHER PUBLICATIONS

Dolgin, "Parkinson's drug makers target inflammasome", Nature Biotechnology, Jan. 2019.
Dong et al., "Collagen cross-linking with riboflavin in a femtosecond laser-created pocket in rabbit corneas: 6-month results", Am J Ophthalmol, Jul. 2011, vol. 152(1), pp. 22-27.e1.
Dorronsoro et al., "Dynamic OCT measurement of corneal deformation by an air puff in normal and cross-linked corneas". Biomedical Optics Express, vol. 3 / Issue 3, pp. 473-487, Feb. 2012.
Durrie et al., "Femtosecond laser versus mechanical keratome flaps in wavefront-guided laser in situ keratomileusis Prospective contralateral eye study", Journal of Cataract & Refractive Surgery, Jan. 1, 2005, vol. 31(1), pp. 120-126.
Esmonde-White et al., "Fiber-optic Raman Spectroscopy of Joint Tissues", Analyst, vol. 136(8), Apr. 21, 2012 [retrieved on Oct. 4, 2017), Retrieved from the Internet.
Esmonde-White et al., "Raman spectroscopy of synovial fluid as a tool for diagnosing osteoarthritis", Journal of Biomedical Optics, vol. 14(3), pp. 034013, May 14, 2009.
Evans et al., "Reactivity of the (1Δg)2 and 1Δg states of oxygen produced by direct laser excitation", Journal of the Chemical Society, Faraday Transactions 2: Molecular and Chemical Physics, vol. 72, pp. 1661-1666, 1976.
Extended Report and Opinion issued in the corresponding EP Application No. 16858413.4 dated Aug. 30, 2018.
Eydelman et al., "Symptoms and satisfaction of patients in the patient-reported outcomes with laser in situ keratomileusis (PROWL) studies", JAMA Ophthalmol, Jan. 1, 2017, vol. 135(1), pp. 13-22.
Eyre et al., "Cross-linking in collagen and elastin", Annual Reviews Biochem, vol. 53, pp. 717-748, 1984.
Eyre, "Collagen cross-linking in skeletal aging and disease", NIH Grant# 5R37AR037318-32, Awardee: University of Washington.
Farah et al., "Laser in situ keratomileusis: literature review of a developing technique", Journal of Cataract & Refractive Surgery, vol. 24(7), pp. 989-1006, 1998.
Farjadnia et al., "Corneal cross-linking treatment of keratoconus", Oman J Ophthalmol, vol. 8(2), pp. 86-91, May 2015.
Felson et al., "Osteoarthritis: new insights. Part 1: the disease and its risk factors", Annals of Internal Medicine, Oct. 17, 2000, vol. 133(8), pp. 635-646.
Filipello et al., "Transepithelial corneal collagen crosslinking: bilateral study", J Cataract Refract Surg, 2012; vol. 38, pp. 283-291.
Final Office Action dated Sep. 30, 2020, issued in U.S. Appl. No. 16/192,364.
Friedman et al., "Advanced corneal cross-linking system with fluorescence dosimetry"; Journal of Ophthalmology, vol. 2012, Article No. 303459, Jul. 2012.
Gallego-Munoz et al., "Corneal Wound Repair After Rose Bengal and Green Light Crosslinking: Clinical and Histologic Study", Invest Ophthalmol Vis Sci, Jul. 1, 2017, vol. 58(9), pp. 3471-3480.
Gil et al., "Improved self-healing properties of collagen using polyurethane microcapsules containing reactive diisocyanate", Polymer International, Apr. 29, 2016, vol. 65(6), pp. 721-727.
Guo et al., "Femtosecond laser collagen cross-linking without traditional photosensitizers", Optical Interactions with Tissue and Cells XXVI, Mar. 5, 2015, vol. 9321, pp. 932103-1-932103-13.
Guo et al., "Investigation of the formation mechanism and morphology of the features created in the interior of cornea by femtosecond laser pulses", Optical Interactions with Tissue and Cells XXVI, Mar. 1, 2015, vol. 9321, pp. 932106-1-932106-14.
Gutierrez-Bonnet et al., "Macular Choroidal Thickening in Keratoconus Patient: Swept-Source Optical Coherence Tomography Study", Translational Vision Science & Technology, vol. 7(3), p. 15, Jun. 2018.
Hardy et al., "The nature of the cross-linking of proteins by glutaraldehyde. Part 2. The formation of quaternary pyridinium compounds by the action of glutaraldehyde on proteins and the identification of a 3-(2-piperidyl)-pyridinium derivative, anabilysine, as a cross-linking entity", Journal of the Chemical Society, Perkin Transactions, 1, pp. 2282-2288, Jan. 1, 1979.

He et al., "Femtosecond laser-assisted cataract surgery", Current Opinion in Ophthalmology, vol. 22(1), pp. 43-52, 2011.
Helena et al., "Keratocyte apoptosis after corneal surgery", Invest Ophthalmol Vis Sci, Feb. 1998, vol. 39(2), pp. 276-283.
Holden et al., "Global prevalence of myopia and high myopia and temporal trends from 2000 through 2050", Ophthalmology, May 2016, vol. 123(5), pp. 1036-1042.
Holzer et al., "Femtosecond laser-assisted corneal flap cuts: morphology, accuracy, and histopathology", Invest Ophthalmol Vis Sci, Jul. 2006, vol. 47(7), pp. 2828-2831.
Hovakimyan et al., "Imaging corneal crosslinking by autofluorescence 2-photon microscopy, second harmonic generation, and fluorescence lifetime measurements", Journal of Cataract & Refractive Surgery, vol. 36(12), pp. 2150-2159, 2010.
Hovhannisyan et al., "Photophysical mechanisms of collagen modification by 80 MHz femtosecond laser", Optics Express, vol. 18(23), pp. 24037-24047, 2010.
International Preliminary Report on Patentability dated Aug. 6, 2020, issued in International Application No. PCT/US2019/015095.
International Preliminary Report on Patentability dated Oct. 8, 2020, issued in International Application No. PCT/US2019/024321.
International Preliminary Report on Patentability for International Application No. PCT/US2016/058353 dated May 3, 2018.
International Preliminary Report on Patentability issued in International Application No. PCT/US2017/036915 dated Dec. 20, 2018.
International Search Report and Written Opinion for International Application No. PCT/US2016/058353 dated Feb. 21, 2017.
International Search Report and Written Opinion for International Application No. PCT/US2017/036915 dated Oct. 23, 2017.
International Search Report and Written Opinion for International Application No. PCT/US2019/015095 dated Apr. 22, 2019.
International Search Report and Written Opinion issued in International Application No. PCT/US2019/040728 and dated Sep. 18, 2019.
International Search Report and Written Opinion dated Feb. 5, 2020 for International Patent Application No. PCT/US2019/063320.
International Search Report and Written Opinion dated Jun. 11, 2019 for International Patent Application No. PCT/US2019/024321.
Jastrzebska et al., "Raman spectroscopic study of glutaraldehyde stabilized collagen and pericardium tissue", Journal of Biomaterials Science, Polymer Edition, vol. 14(2), pp. 185-197, Apr. 2, 2003.
Jester et al., "Non-Linear Optical Collagen Cross-Linking (NLO CXL) for Treatment of Keratoconus", Project No. 5R01EY024600-04, Jul. 31, 2019.
Jirasek et al., "Accuracy and Precision of Manual Baseline Determination", Applied Spectroscopy, 58012, pp. 1488-1499, 2004.
John, A Wide-Angle View of Keratoconus, ,Review of Optometry, Oct. 2012, pp. 1-5.
Jones et al., "Nanoscale dysregulation of collagen structure-function disrupts mechano-homeostasis and mediates pulmonary fibrosis", eLife, vol. 7, pii: e36354, Jul. 2018.
Juhasz et al., "Corneal refractive surgery with femtosecond lasers", IEEE Journal of Selected Topics in Quantum Electronics, vol. 5(4), pp. 902-910, 1999.
Juhasz et al., "Time-resolved observations of shock waves and cavitation bubbles generated by femtosecond laser pulses in corneal tissue and water", Lasers in Surgery and Medicine, Jan. 1, 1996, vol. 19(1), pp. 23-31.
Kanellopoulos et al., "Collagen cross-linking (CCL) with sequential topography-guided PRK: a temporizing alternative for keratoconus to penetrating keratoplasty", Cornea, vol. 26(7), pp. 891-895, 2007.
Kanellopoulos et al., "Epithelial Remodeling After Femtosecond Laser-assisted High Myopic LASIK: Comparison of Stand-alone With LASIK Combined With Prophylactic High-fluence Crosslinking", Cornea, vol. 33(5), May 2014, pp. 463-469.
Kanellopoulos et al., "Topography-guided Hyperopic LASIK With and Without High Irradiance Collagen Cross-linking Initial Comparative Clinical Findings in a Contralateral Eye Study of 34 Consecutive Patients", Journal of Refractive Surgery, vol. 28 / Issue 11, pp. S837-S840, Nov. 2012.

(56) References Cited

OTHER PUBLICATIONS

Kanellopoulos, "Collagen cross-linking in early keratoconus with riboflavin in a femtosecond laser-created pocket: Initial clinical results", J Retract Surg,. 2009; vol. 25, pp. 1034 1037.
Karamburoglu et al., "Intacs implantation with sequential collagen cross-linking treatment in postoperative LASIK ectasia."; J Refract Surg, 2008, vol. 24, S726-S729.
Kato et al., "Topography-Guided Conductive Keratoplasty: Treatment for Advanced Keratoconus", American Journal of Ophthalmology, Oct. 1, 2010, vol. 150(4), pp. 481-489.
Kempen et al., "The prevalence of refractive errors among adults in the United States, Western Europe, and Australia", Arch Ophthalmol., Apr. 2004, vol. 122(4), pp. 495-505.
Kermani et al., "Comparative micromorphologic in vitro porcine study of IntraLase and femto LDV femtosecond lasers."; J Cataract Refract Surg, 2008, vol. 34, 1393-1399.
Kilic et al., "Riboflavin injection into the corneal channel for combined collagen crosslinking and intrastromal corneal ring segment implantation."; J Cataract Refract Surg, 2012,vol. 38, pp. 878-883.
Kling et al., "Corneal biomechanical changes after collagen cross-linking from porcine eye inflation experiments", Invest Ophthalmol & Vis Sci, vol. 51(8), pp. 3961-3968, Aug. 2010.
Kolli et al., "Safety and efficacy of collagen crosslinking for the treatment of keratoconus", Expert Opinion on Drug Safety, vol. 9(6), pp. 949-957, 2010.
Konig et al., "Intratissue surgery with 80 MHz nanojoule femtosecond laser pulses in the near infrared", Optics Express, Feb. 11, 2002, vol. 10(3), pp. 171-176.
Krueger et al., "Staged intrastromal delivery of riboflavin with UVA cross-linking in advanced bullous keratopathy laboratory investigation and first clinical case", J Refract Surg, 2008, vol. 24, pp. S730-S736.
Kumar et al., "A double-blind, placebo-controlled, randomised, clinical study on the effectiveness of collagen peptide an osteoarthritis", Journal Science of Food and Agriculture, vol. 95(4), pp. 702-707, Mar. 15, 2015.
Kwok et al., "Selective two-photon collagen crosslinking in situ measured by Brillouin microscopy". Optica, May 20, 2016, vol. 3(5), pp. 469-472.
Kymionis et al., "Simultaneous topography-guided PRK followed by corneal collagen cross-linking for keratoconus", Journal of Refractory Surgery, vol. 25(9), pp. S807-822, Sep. 2009.
Leccisotti et al., "Transepithelial corneal collagen cross-linking in keratoconus", J Refract Surg, 2010, vol. 26, pp. 942-948.
Leger et al., "Comparison of Derivative Preprocessing and Automated Polynomial Baseline Correction Method for Classification and Quantification of Narcotics in Solid Mixtures"; Society for Applied Spectroscopy; vol. 60(2); pp. 182-193, 2006.
Legrand et al., "Glycation Marker Glucosepane Increases with the Progression of Osteoarthritis and correlates with Morphological and Functional changes of Cartilage in vivo", Arthritis Research & Therapy, vol. 20(1), p. 131, Jun. 2018.
Letnikova et al., "Femtosecond Corneal Collagen Crosslinking in Treatment of Patients with Progressive Keratoconus Stages I-II", Clinical and Translational Medicine, 2016 (full date not available), vol. 8(1), pp. 128-132.
Lim et al.; "Epithelium-on photorefractive intrastromal cross-linking (PiXL) for reduction of low myopia"; Clin Ophthalmol, 2017; vol. 11, pp. 1205-1211.
Liu et al., "Corneal Epithelial Wound Healing", Progress in Molecular Biology and Translational Science, Academic Press, vol. 134, 2015, pp. 61-71.
Lombardo et al., "Biomechanics of the anterior human corneal tissue investigated with atomic force microscopy." Invest Ophthalmol Vis Sci, 2012; vol. 53, pp. 1050-1057.
Lubatschowski et al., "Application of ultrashort laser pulses for intrastromal refractive surgery", Graefe's Archive for Clinical and Experimental Ophthalmology, vol. 238(1), pp. 33-39, 2000.

Luz et al., "Application of corneal tomography before keratorefractive procedure for laser vision correction", Journal of Biophotonics, vol. 9 / Issue 5, pp. 445-453, Apr. 2016.
Marshall et al., "Long-term healing of the central cornea after photorefractive keratectomy using an excimer laser", Ophthalmology, vol. 95(10), pp. 1411-1421, 1988.
Matheson et al., "The quenching of singlet oxygen by amino acids and proteins", Photochemistry and Photobiology, vol. 21(3), pp. 165-171, 1975.
Mayo et al., "Course notes on the interpretation of infrared and Raman spectra"; John Wiley & Sons, Inc., 2003.
Mazet et al., "Background removal from spectra by designing and minimising a non-quadratic cost function", Chemometrics and Intelligent Laboratory Systems, vol. 76, 2005, pp. 121-133.
Medeiros et al., "Biomechanical corneal changes induced by different flap thickness created by femtosecond laser." Clinics (Sao Paulo), 2011, vol. 66, pp. 1067-1071.
Meek et al., "Corneal cross-linking—a review", Ophthal Physiol Optics. Feb. 2013; 33(2): pp. 78-93.
Meier, "On art and science in curve-fitting vibrational spectra", Vibrational Spectroscopy; vol. 39(2), pp. 266-269, Mar. 10, 2005.
Meltendorf et al., "Corneal intrastromal tissue modeling with the femtosecond laser", Graefes Archive for Clinical and Experimental Ophthalmology, Nov. 1, 2011, vol. 249(11), pp. 1661-1666.
Migneault et al., "Glutaraldehyde: behavior in aqueous solution, reaction with proteins, and application to enzyme crosslinking", BioTechniques, vol. 3, pp. 790-802, Nov. 2004.
Mittal et al., "Reactive oxygen species in inflammation and tissue injury", Antoxid Redox Signal, Oct. 2013, vol. 20(7), pp. 1126-1167.
Morishige et al., "Quantitative Analysis of Collagen Lamellae in the Normal and Keratoconic Human Cornea by Second Harmonic Generation Imaging Microscopy", Investigative Ophthalmology & Visual Science, Dec. 2014, vol. 55, pp. 8377-8385.
Munnerlyn et al., "Photorefractive keratectomy: a technique for laser refractive surgery", Journal of Cataract & Refractive Surgery, vol. 14(1), pp. 46-52, 1988.
Netto et al., "Wound healing in the cornea: a review of refractive surgery complications and new prospects for therapy", Cornea, Jul. 2005, vol. 24(5), pp. 509-522.
Nguyen et al., "Corneal collagen cross-linking in the stabilization of PRK, LASIK, thermal keratoplasty, and orthokeratology", Current Opinion in Ophthalmology, Jul. 1, 2013, vol. 24(4), pp. 291-295.
Nikogosyan et al., "Two-Photon Ionization and Dissociation of Liquid Water by Powerful Laser UV Radiation", Chemical Physics 77 (1983) 131-143, pp. 131-143.
Nover et al., "Long-term storage and preservation of tissue engineered articular cartilage", J Orthop Res, Jan. 2016, vol. 34(1), pp. 141-148.
Office Action (Communication Pursuant to Article 94(3) EPC) dated Nov. 14, 2019 for European Patent Application No. 16858413.4.
Park et al., "Second Harmonic Generation Imaging Analysis of Collagen Arrangement in Human Cornea", Investigative Ophthalmology & Visual Science, vol. 56(9), pp. 5622-5629, 2015.
Patel et al., "Keratocyte progenitor cell transplantation: A novel therapeutic strategy for corneal disease", Medical Hypotheses, vol. 80(2), pp. 122-124, Feb. 2013.
Pedrigi et al., "Regional mechanical properties and stress analysis of the human anterior lens capsule", Vision Research, vol. 47 / Issue 13, pp. 1781-1789, Jun. 2007.
Poli et al., "Prospective study of corneal collagen cross-linking efficacy and tolerance in the treatment of keratoconus and corneal ectasia: 3-year results". Cornea, 2013, vol. 32, pp. 583-590.
Price et al., "Photoactivated riboflavin treatment of infectious keratitis using collagen cross-linking technology", Journal of Refractive Surgery, vol. 28(10), pp. 706-713, Oct. 2012.
Rabinowitz, "Keratoconus", Survey of Ophthalmology, Jan.-Feb. 1998, vol. 42(4), pp. 297-319.
Raiskup-Wolf et al., "Collagen crosslinking with riboflavin and ultraviolet-A light in keratoconus: Long-term results", Journal of Cataract & Refractive Surgery, vol. 34 (5), May 1, 2008, pp. 796-801.

(56) References Cited

OTHER PUBLICATIONS

Rapuano et al., "Antimicrobial Studies Using the Therapeutic Tissue Cross-Linking Agent, Sodium Hydroxymethylglycinate: Implication for Treating Infectious Keratitis", IOVS, vol. 59(1), pp. 332-337, Jan. 2018.
Reddy et al., "Laser photostimulation of collagen production in healing rabbit achilles tendons", Lasers in Surgery and Medicine, Jan. 1, 1998, vol. 22(5), pp. 281-287.
Ricard-Blum et al., "Collagen Cross-Linking"; Int. J. Biochem, vol. 21(11), pp. 1185-1189, Apr. 27, 1989.
Rich et al., "The Molecular Structure of Collagen"; J Mol Biol, 1961, vol. 3; pp. 483-506; Feb. 23, 1961.
Rocha et al., "Comparative study of riboflavin-UVA cross-linking and "flash-linking" using surface wave elastometry," Journal of Refractive Surgery, Sep. 1, 2008, vol. 24(7), pp. S748-S751.
Romero-Jimenez et al., "Keratoconus: a review. Contact Lens and Anterior Eye", vol. 33(4), pp. 157-166, 2010.
Rossi et al., "Modeling the load resistance in laser-assisted cornea transplantation", Proceedings of SPIE: Ophthalmic Technologies, vol. 10858, Feb. 2019.
Saarakkala et al., "Specificity of Fourier Transform Infrared (FTIR) microspectroscopy to estimate depth wise proteoglycan content in normal and osteoarthritic human articular cartilage", Cartilage, Oct. 2010, vol. 1(4), pp. 262-269.
Sagoo et al., "Inflammatory Cytokines Induce Apoptosis of Corneal Endothelium through Nitric Oxide"; Investigative Ophthalmology & Visual Science, Nov. 2004, vol. 45, pp. 3964-3973, doi:10.1167/iovs.04-0439.
Sakimoto et al., "Laser eye surgery for refractive errors", The Lancet, Apr. 29, 2006, vol. 367(9520), pp. 1432-1447.
Salamão et al., "Corneal wound healing after ultraviolet-A/riboflavin collagen cross-linking: a rabbit study", J Refract Surg, Jun. 2011, vol. 27(6), pp. 401-407, doi: 10.3928/1081597X-20101201-02. Epub Dec. 1, 2010.
Schallhorn, "Outcomes of wavefront-guided laser in situ keratomileusis using a new-generation Hartmann-Shack aberrometer in patients with high myopia", Journal of Cataract & Refractive Surgery, vol. 41(9), Sep. 2015, pp. 1810-1819.
Schumacher et al., "Absorption of UV-light by riboflavin solutions with different concentration", J Refract Surg, 2012, vol. 28, pp. 91-92.
Sharif et al., "Human in vitro Model Reveals the Effects of Collagen Cross-linking on Keratoconus Pathogenesis", Scientific Reports, vol. 7(1), Oct. 2017.
Shen, "Photodisruption in biological tissues using femtosecond laser pulses", Diss Harvard University, Cambridge, Massachusetts, 2003.
Shetty et al., "Collagen crosslinking in the management of advanced non-resolving microbial keratitis", Br J Opthalmol, Aug. 2014, vol. 98(8), pp. 1033-1055.
Sidhu et al., "Femtosecond laser-assisted selective reduction of neovascularization in rat cornea", Lasers in Medical Science, Jul. 1, 2014, vol. 29(4), pp. 1417-1427.
Singh et al., "Possible formation of singlet oxygen from vibrationally excited water", Journal of Photochemistry vol. 25(2), pp. 99-104, 1984.
Søndergaard et al., "Corneal distribution of riboflavin prior to collagen cross-linking"; Current Eye Research, 2010, vol. 35, pp. 116-121.
Song et al., "Viability, apoptosis, proliferation, activation, and cytokine secretion of human keratoconus keratocytes after crosslinking", Biomedical Research International, Epub 2015:253237, Jan. 2015.
Sorkin et al., "Corneal Collagen Crosslinking: A Systematic Review" Ophthalmologica, vol. 232, Apr. 2014, pp. 10-27.
Spoerl et al., "Corneal Cross-Linking and Safety Issues", The Open Ophthalmology Journal, Feb. 2011, vol. 5, pp. 14-16.
Spoerl et al., "Induction of cross-links in corneal tissue", Experimental Eye Research, Jan. 1, 1998, vol. 66(1), pp. 97-103.
Spoerl et al., "Thermomechanical behavior of collagen-cross-linked porcine cornea", Ophthalmologica, vol. 218(2), pp. 136-140, 2004.
Stantchev et al., "Subwavelength hyperspectral THz Studies of Articular Cartilage", Scientific Reports, vol. 8, Published online May 2, 2018.
Tabibian et al., "PACK-CXL: Corneal Cross-linking for Treatment of Infectious Keratitis", Journal of Ophthalmic & Vision Research, vol. 10(1), pp. 77-80, Jan. 2015.
Tait et al., "Fourier transform Raman spectroscopic examination of two amine-based epoxy resin crosslinking agents"; Elsevier, Spectrochimica Acta Part A, vol. 51, pp. 2101-2106, 1995.
Takahashi et al., "Raman spectroscopy investigation of load-assisted microstructural alterations in human knee cartilage: Preliminary study into diagnostic potential for osteoarthritis", Journal of the Mechanical Behavior of Biomedical Materials, vol. 31, pp. 77-86, Mar. 4, 2014.
Turner, "Laser Vision Correction: A Tutorial for Medical Students," Eye Rounds.org, 2011, pp. 1-7, University of Iowa Health Care, Iowa City, Iowa.
Turunen et al., "Pico- and femtosecond laser-induced crosslinking of protein microstructures: evaluation of processability and bioactivity", 2011 Biofabrication 3 045002 (http://iopscience.iop.org/1758-5090/3/4/045002), downloaded Oct. 9, 2011, pp. 1-14.
Unknown, "New Method Could Offer More Precise Treatment for Corneal Disease", The Optical Society, May 4, 2016.
Unknown, "New noninvasive reflective treatment on the horizon", EyeWorld, Oct. 2018.
Vaddavalli et al., "Air bubble in anterior chamber as indicator of full-thickness incisions in femtosecond-assisted astigmatic keratotomy", Journal of Cataract & Refractive Surgery, Sep. 1, 2011, vol. 37(9), pp. 1723-1725.
Vazirani et al., "Keratoconus: current perspectives", Clinical Ophthalmology, Oct. 2013, vol. 7, pp. 2019-2030.
Vinciguerra et al., "Corneal collagen crosslinking for ectasia after excimer laser refractive surgery: 1-year results", J Refract Surg, 2010, vol. 26, pp. 486-497.
Vogel et al., "Low-Density Plasma Below the Optical Breakdown Threshold—Potential Hazard for Multiphoton Microscopy, and a Tool for the Manipulation of Intracellular Events", Proc. SPIE, vol. 4620, Multiphoton Microscopy in the Biomedical Sciences II, 2002, 15 pages.
Vukelic et al., "Investigation of the morphology of the features generated via femtosecond lasers in the interior of a bovine cornea sections", SPIE Proceedings, vol. 8579, Optical Interactions with Tissue and Cells XXIV, 857904, Feb. 15, 2013, 10 pages.
Vukelic et al., "Ultrafast Laser Induced Structural Modification of Fused Silica—Part II: Spatially Resolved and Decomposed Raman Spectral Analysis", Journal of Manufacturing Science and Engineering, vol. 132(6), pp. 0361013-1-061013-9, Dec. 2010.
Wang et al., "A New Paradigm for Use of Ultrafast Lasers in Ophthalmology for Enhancement of Corneal Mechanical Properties and Permanent Correction of Refractive Errors", Proc of SPIE, vol. 10066, Energy-based Treatment of Tissue and Assessment IX, 100660Y, Feb. 2017.
Wang et al., "Femtosecond laser crosslinking of the cornea for non-invasive vision correction", Nature Photonics, vol. 12, pp. 416-422, May 2018.
Wang et al., "Femtosecond Laser Irradiation as Novel Paradigm for Treatment of Early Osteoarthritis", Annual Meeting of the Orthopaedic Research Society, San Diego, CA, USA, 2017.
Wang et al., "Near-infrared Femtosecond Laser as a potential Tool for non- invasive Refractive Error Corrections", In preparation (2017).
Wang et al., "Quantitative analysis of Raman spectra for assessment of cross link concentrations toward diagnosing early osteoarthritis", Summer Biomechanics, Bioengineering and Biotransport Conference, Snowbird, UT, USA, 2015.
Wang et al., "Quantitative Raman characterization of cross-linked collagen thin films as a model system for diagnosing early osteoarthritis", SPIE BiOS, International Society for Optics and Photonics, 970415-970415, 2016.

(56) References Cited

OTHER PUBLICATIONS

Wang, Chao, et al., "Femtosecond laser crosslinking of the cornea for non-invasive vision correction", Nature Photonics 12.7 (2018); https://doi.org/10.1038/S41566-018-017 4-8.
Wei et al., "Comparison of corneal sensitivity between FS-LASIK and femtosecond lenticule extraction (ReLEx flex) or small-incision lenticule extraction (ReLEx smile) for myopic eyes", Graefes Archive for Clinical and Experimental Ophthalmology, Feb. 7, 2013, vol. 251(6), pp. 1645-1654.
Wei et al., "Erratum to: Comparison of corneal sensitivity between FS-LASIK and femtosecond lenticule extraction (ReLEx flex) or small-incision lenticule extraction (ReLEx smile) for myopic eyes", Graefes Archive for Clinical and Experimental Ophthalmology, May 1, 2013, vol. 251, pp. 2495-2497.
West et al., "Fourier Transform Infrared Spectral Analysis of Degenerative Cartilage: An Infrared Fiber Optic Probe and Imaging Study"; Applied Spectroscopy, vol. 58(4), pp. 376-381, 2004.
Wilkinson et al., "Refractive eye surgery: helping patients make informed decisions about LASIK", Am Fam Physician, May 15, 2017, vol. 95(10), pp. 637-644.
Wilson et al., "Epithelial injury induces keratocyte apoptosis: hypothesized role for the interleukin-1 system in the modulation of corneal tissue organization and wound healing", Exp Eye Res, Apr. 1996, vol. 62(4), pp. 325-327.
Wilson et al., "Herpes simplex virus type-1 infection of corneal epithelial cells induces apoptosis of die underlying keratocytes", Exp Eye Res, 1997, vol. 64, pp. 775-779.
Wisse et al., "Cytokine Expression in Keratoconus and its Corneal Microenvironment: A Systematic Review", The Ocular Surface, Oct. 2015, vol. 13(4), pp. 272-283.
Wollensak et al., "Biomechanical and histological changes after corneal crosslinking with and without epithelial debridement", Journal of Cataract & Refractive Surgery, vol. 35(3), pp. 540-546, 2009.
Wollensak et al., "Biomechanical Efficacy of Collagen Crosslinking in Porcine Cornea Using a Femtosecond Laser Pocket", Cornea, Mar. 1, 2014, vol. 33(3), pp. 300-305.
Wollensak et al., "Hydration behavior of porcine cornea crosslinked with riboflavin and ultraviolet A", J Cataract Refract Surg, 2007, vol. 33, pp. 516-521.
Wollensak et al., "Interlamellar cohesion after corneal collagen crosslinking using riboflavin and ultraviolet A light", Br J Ophthalmol, 2011, vol. 95, pp. 876-880.
Wollensak et al., "Long-term biomechanical properties of rabbit cornea after photodynamic collagen crosslinking", Acta Ophthalmologica, vol. 87(1), pp. 48-51, 2009.
Wollensak et al., "Riboflavin/ultraviolet-A-induced collagen crosslinking for the treatment of keratoconus", Am J Ophthalmol, 2003, vol. 135, pp. 620-627.
Wollensak, "Corneal collagen crosslinking: new horizons", Expert Rev Ophthalmol, 2010, vol. 5, pp. 201-215.
Wollensak, "Crosslinking treatment of progressive keratoconus: new hope", Current Opinion in Ophthalmology, vol. 17(4), pp. 356-360, 2006.
Xia et al., "Corneal collagen fibril changes after ultraviolet a/riboflavin corneal crosslinking", Cornea, vol. 33(1), pp. 56-59, Jan. 2014.
Xia et al., "Low-intensity pulsed ultrasound treatment at an early osteoarthritis stage protects rabbit cartilage from damage via the integrin/focal adhesion kinase/mitogen-activated protein kinase signaling pathway", Journal of Ultrasound in Medicine, Nov. 1, 2015, vol. 34(11), pp. 1991-1999.
Xia et al., "The depth-dependent anisotropy of articular cartilage by Fourier transform infrared imaging (FTIRI)", Osteoarthritis and Cartilage, vol. 15, pp. 780-788, 2007.
Xie et al., "Robust increase of cutaneous sensitivity, cytokine production and sympathetic sprouting in rats with ocalized inflammatory irritation of the spinal ganglia", Neuroscience, Nov. 2006, vol. 142(3), pp. 809-822.
Zaitsev et al., "Optical coherence elastography for strain dynamics measurements in laser correction of cornea shape", Journal of Biophotonics, vol. 10 / Issue 11, pp. 1450-1463, 2017.
Zayed et al., "Xenogenic Implantation of Equine Synovial Fluid-Derived Mesenchymal Stem Cells Leads to Articular Cartilage Regeneration", Stem Cells Int, Jun. 2018.
Zhang et al., "Cytokines, inflammation and pain", Int Anesthesiol Clin, Nov. 2009, vol. 45(2), pp. 27-37.
Zhao et al., "Automated Autofluorescence Background Subtraction Algorithm for Biomedical Raman Spectroscopy", Applied Spectroscopy, First Published Nov. 1, 2007, vol. 61(11), pp. 1225-1232.
Zhu et al., "Corneal Crosslinking With Rose Bengal and Green Light: Efficacy and Safety Evaluation", Cornea,. Sep. 2016, vol. 35(9), pp. 1234-1241.
Zipfel et al., "Live tissue intrinsic emission microscopy using multiphoton-excited native fluorescence and second harmonic generation", Proceedings of the National Academy of Sciences, vol. 100(12), pp. 7075-7080, 2003.

\* cited by examiner

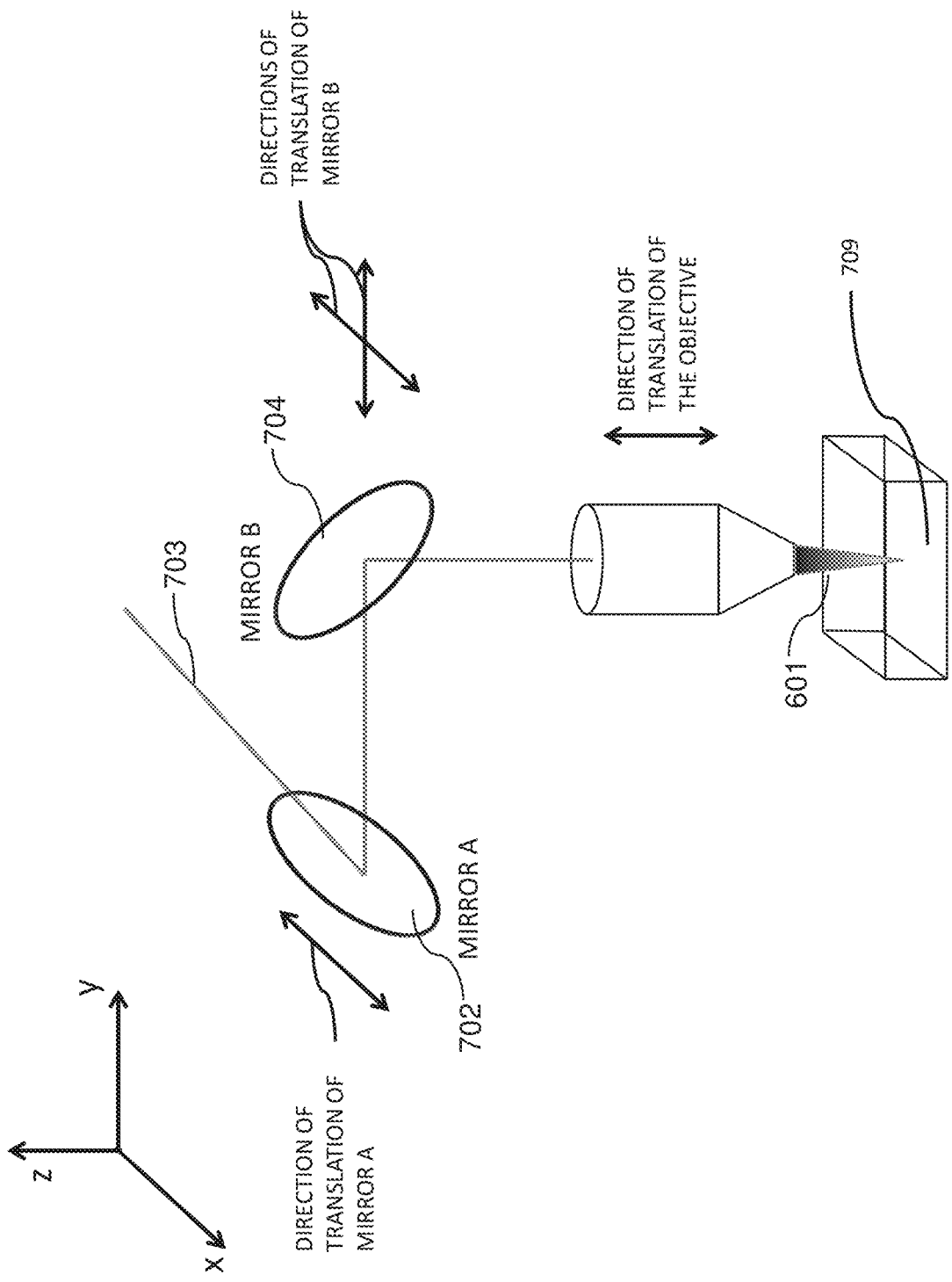

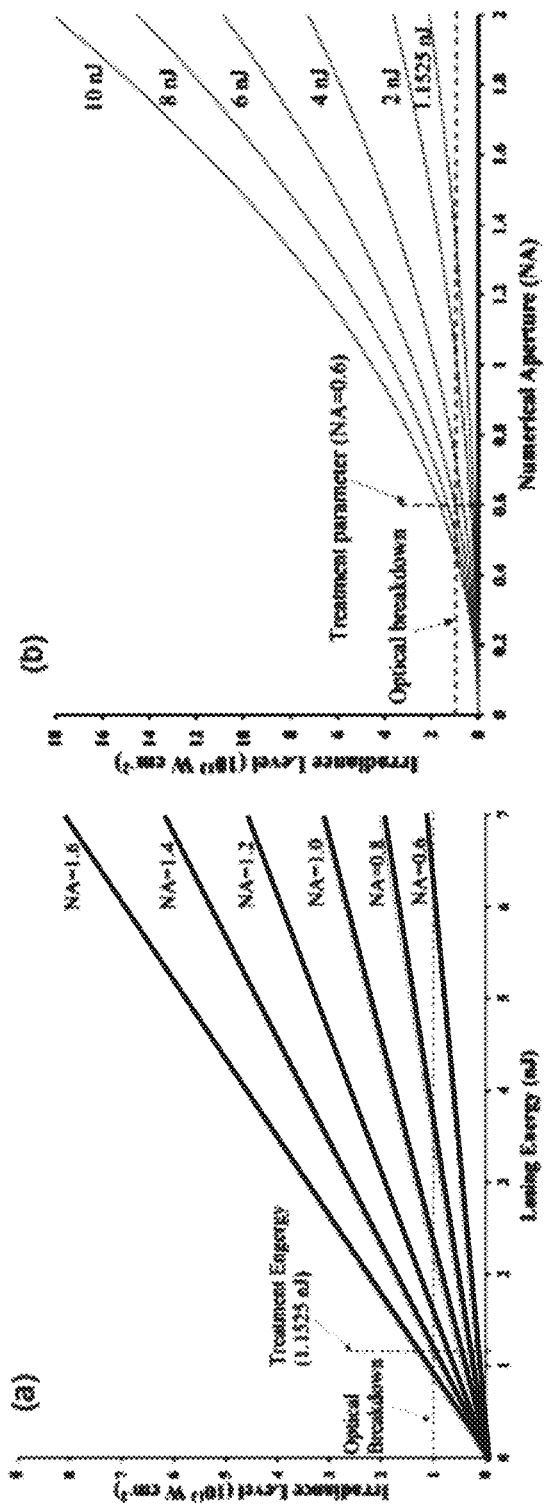

Figure 18 (a) The average lasing energy vs treatment lasing irradiance level curves. The optical breakdown is approximately $1.0 \times 10^{13}$ W cm$^{-2}$ and the corresponding average energy intensity for the applied laser would be 0.319 W, while the treatment applied an average energy 1.1525 nJ and the corresponding irradiance level is round $0.19 \times 10^{13}$ W cm$^{-2}$. (b) The objective numerical aperture vs treatment lasing irradiance level curve. The optical breakdown is approximately $1.0 \times 10^{13}$ W cm$^{-2}$ and numerical aperture required to achieve optical breakdown at treatment irradiance is 1.384.

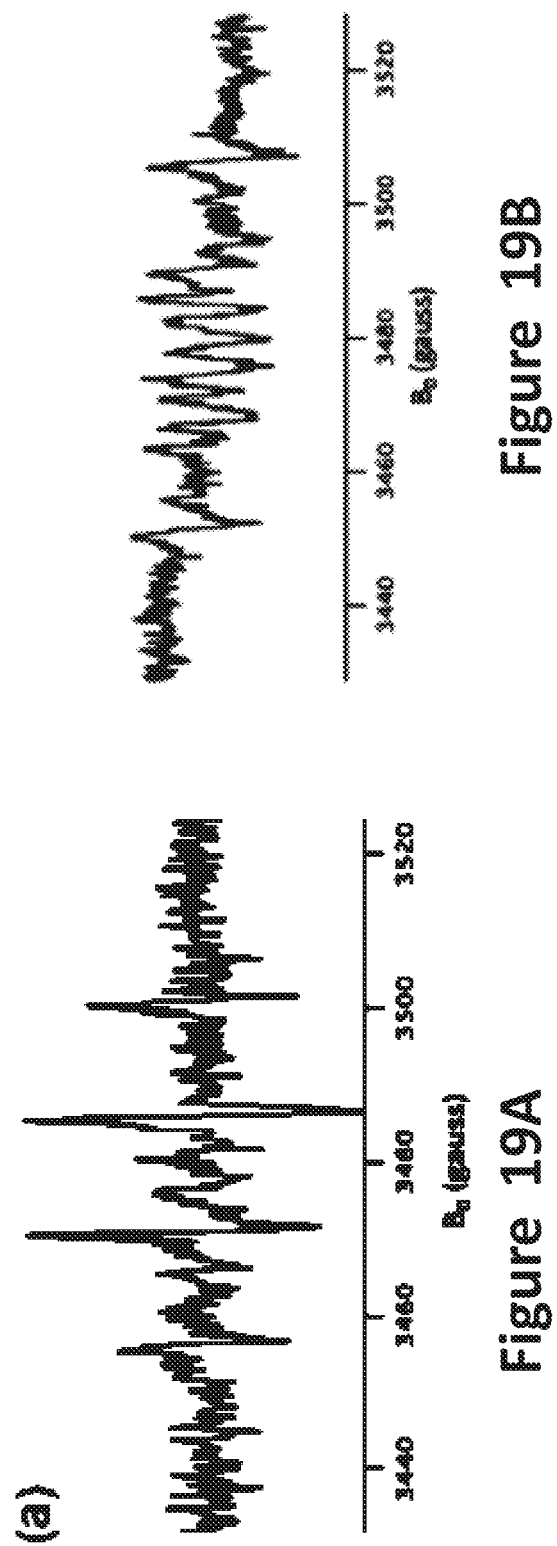

LASER INDUCED COLLAGEN CROSSLINKING IN TISSUE

CROSS-REFERENCE TO RELATED APPLICATIONS

This application is a continuation of U.S. application Ser. No. 15/893,264, filed on Feb. 9, 2018, which is a U.S. national stage filing under 35 U.S.C. § 371 of International Application No. PCT/US2016/058353 filed Oct. 23, 2016, which claims priority to U.S. provisional application 62/245,805 filed on Oct. 23, 2015; U.S. provisional application 62/358,035 filed on Jul. 3, 2016; and U.S. provisional application 62/380,713 filed on Aug. 29, 2016. The entire contents of each of the above applications is hereby expressly incorporated by reference.

BACKGROUND

Collagen is an abundant protein in animals. The mechanical properties and structural stability of collagen based tissues, such as cartilage, tendons, ligaments, or corneal stroma, can be influenced by increasing collagen cross-links (CXL), in the form of intra or inter molecule chemical bonds. CXL are naturally formed in tissues, but inducing new or additional CXL can be beneficial. Strength and the ability to bend under tension are two characteristics of collagen, which is the significant component in ligaments and tendons. Ligaments bind bones to bones while tendons bind muscles to bones. The strength and flexibility of collagen provides for ease of movement. Strength and flexibility are also two characteristics of cartilage, which covers the ends of bones at a joint. Cartilage allows one bone to glide over another as it protects and prevents bones from rubbing against each other.

BRIEF SUMMARY

The presently disclosed subject matter provides techniques for inducing collagen cross-linking in human tissue, such as cartilage or cornea, or skin, without using a photosensitizer (e.g., riboflavin). While laser light at any frequency can be used, in some embodiments a laser outside of the ultraviolet (UV) frequency band is used. In an embodiment, a femtosecond laser operates at sufficiently low laser pulse energy to avoid optical breakdown of tissue. In an embodiment, the femtosecond laser operates in the infrared frequency range.

Advances in femtosecond lasers enable using femtosecond laser emitting visible wavelength to ionize liquid water. Femtosecond pulsed lasers also enable direct observation of products of water ionization and dissociation and other aqueous media.

It has been experimentally shown that a scenario, low-density plasma is formed, and treatment is reduced to ionization and dissociation of the water content within the focal volume. This treatment also results in production of reactive oxygen species. Advantageously, the producing of reactive oxygen causes has a disinfecting effect. Initially, ionization of the water molecule occurs, and the ejected electron is quickly hydrated resulting in formation of a solvated electron. Further, the cation radical of water, $H_2O+$, is rather unstable and reacts with a water molecule producing hydrogen ion $H_3O^+$, and hydroxyl radical $OH^*$. Concurrently dissociation of the excited water molecule occurs $H_2O^* \rightarrow H+OH^*$, though other reactive oxygen species may also be produced.

This disclosure expands use of low-density-plasma from sub-cellular level to a microscale. Scaling up has potential to enable microscopic alteration of the chemical composition of target material. In some embodiments, the target material is connective tissue in the human body. In an exemplary embodiment, the tissue is corneal tissue, which in turn results in overall changes of its properties. In other embodiments, the target material is a cartilage. In other embodiments the tissue is tendon, ligament, or corneal stroma. A femtosecond oscillator coupled with an optical delivery system can be adjusted in such a way to deliver local, spatially resolved alteration of chemical composition of tissue without any harmful influences of thermal stresses, such as collagen denaturation. In the case of ocular media, corneal hazing can be avoided.

In embodiments of the disclosed subject matter, the tissue is strengthened selectively to correct defects. In the case of cornea, defects such as keratoconus can be corrected by strengthening the cornea. In further embodiments, the corneal curvature is modified to correct vision problems such as myopia. In still further embodiments, cartilage is treated with a laser to induce cross-linking and thereby strengthen the cartilage. The strengthening of cartilage can slow the progression of, or reverse osteoarthritis.

In embodiments, a laser is scanned over a selected three-dimensional region, which may be a continuous region or a discontinuous region of the cornea to be modified to generate a selected shape change. In a method, the cornea shape is measured and then a pattern of illuminations selected to change the shape of the cornea toward a target is generated in a controller database. In embodiments, the laser can be a femtosecond laser. In embodiments, the femtosecond laser can be a Nd:Glass femtosecond laser. In embodiments, the femtosecond laser can output an average power from about 10 mW to about 100 mW. In embodiments, the femtosecond laser can have a pulse energy of from about 0.1 nJ to about 10 nJ. In embodiments, the cornea can receive from about 10 mW to about 100 mW infrared irradiation from the light source.

In embodiments, the laser can be scanned in a pattern of exposure comprising a circle, annulus, and/or ellipse. The laser can be scanned in multiple layers of the cornea.

According to another aspect of the disclosed subject matter, systems of reshaping curvature of are cornea are provided. In embodiments, an example system of reshaping curvature of a region of a cornea having an initial curvature can include illumination optics configured to project an illumination pattern onto at least a portion of the cornea and a camera configured to record a pattern reflection from the at least a portion of the cornea. The system can also include a control system, coupled to the camera, configured to convert the pattern reflection to a corneal topography, and configured to compare the corneal topography to a desired corneal topography to determine a deformation map 302. The system can further include a laser system, configured to induce ionization in the region of the cornea according to the deformation map 301 to reshape the region from the initial curvature to a new curvature and a coupling device, configured to stabilize the laser system with respect to the cornea.

In embodiments, the laser system is configured to induce cross-linking of collagen in the cornea according to the deformation map. In embodiments, the laser system can include a femtosecond laser. The femtosecond laser can have a pulse width of from about 50 to 150 femtoseconds (fs). The femtosecond laser can have an average power from about 10 mW to about 100 mW. The femtosecond laser can irradiate light in the wavelength range from about 600 nm to about 1100 nm.

In embodiments, the laser system includes a high magnification objective lens and a galvanometer configured to raster a laser beam. The laser system can further include an attenuator.

According to another aspect of the disclosed subject matter, an apparatus for adapting a laser system for reshaping curvature of a region of a cornea having an initial curvature is provided. In embodiments, an example apparatus can include a control system, adapted to be coupled to the laser system and configured to compare an existing corneal topography of at least a portion of the cornea to a desired corneal topography to determine a deformation map. The system can further include laser modification optics, coupled to the control system and configured to adjust laser output of the laser system, to modify a region of the cornea according to the deformation map.

Additional features and advantages of the application will be described hereinafter which form the subject of the claims.

In embodiments, the laser system is adapted to induce cross-linking in connective tissue, such as cartilage.

In embodiments, the laser system and the regime of controlling the output of the system irradiates connective tissue such that the wavelength of the laser is not absorbed by the targeted tissue itself, but rather by water in and around the tissue. Thus, optical breakdown of the tissue is avoided, but the laser is controlled to cause ionization of the water molecules, which in turn generates free radicals which then induce cross-linking in the tissue. This approach is different from directly inducing cross-linking in tissue, because tissues generally absorb only a limited set of wavelengths, which would limit the implementation of treatment system. Conversely, water can be ionized by a broad spectrum of wavelengths to generate free radicals and to avoid breakdown of the targeted tissue.

BRIEF DESCRIPTION OF THE DRAWINGS

FIG. 7C illustrates a diagram of an exemplary scanning objectives system.

FIGS. 18A-18B illustrate a plot of average lasing energy and numerical aperture against irradiance level of an embodiment.

FIGS. 19A-19B illustrate results obtained via electro paramagnetic resonance spectroscopy of an embodiment.

DESCRIPTION

Figure 1:
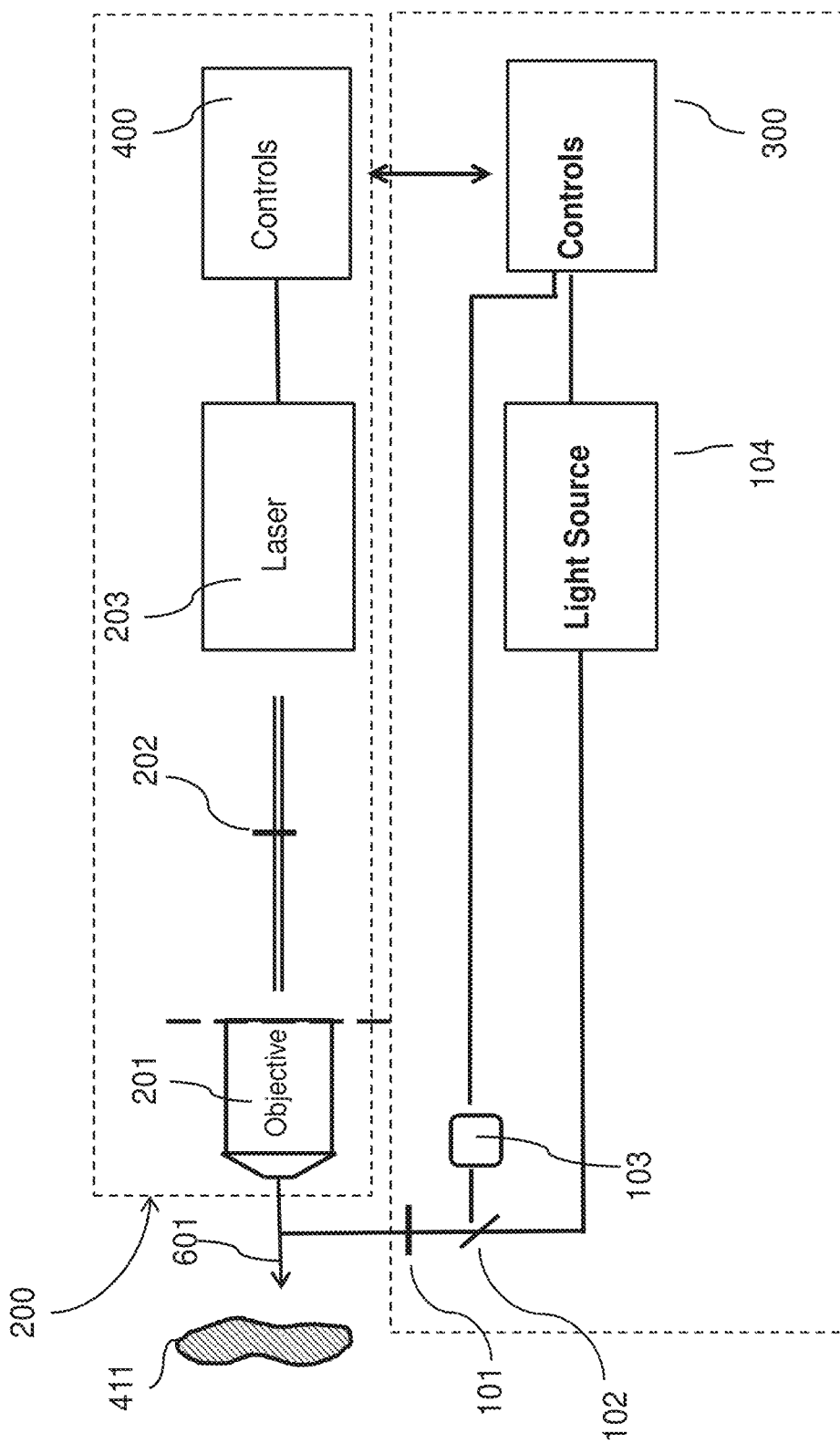
FIG. 1 illustrates a diagram of an exemplary system in accordance with the disclosed subject matter.

The presently disclosed subject matter provides methods and systems for inducing collagen cross-linking in tissues. In embodiments, the focused laser light provides strengthening of the corneal collagen and modification of the corneal curvature. The cross-linking is induced by inducing ionization in the tissue. The ionization can be induced by a laser and can create cross-links. Specifically, ionization of water in or around the tissue generates free radicals which in turn induce cross-linking in the tissue, without optical breakdown in the tissue.

A femtosecond oscillator coupled with an optical delivery system can be adjusted in such a way to deliver local, spatially resolved alteration of chemical composition of ocular media without any harmful influences of thermal stresses, such as collagen denaturation and corneal hazing. A low-density plasma is formed in response to irradiation of a target area by the optical delivery system, and treatment is reduced to ionization and dissociation of the water content within the focal volume. This treatment results in production of reactive oxygen species. Initially, ionization of the water molecule occurs, and the ejected electron is quickly hydrated resulting in formation of a solvated electron. Further, the cation radical of water, $H_2O+$, is rather unstable and react with a water molecule producing hydrogen ion $H_3O^+$, and hydroxyl radical $OH*$. Concurrently dissociation of the excited water molecule occurs $H_2O* \rightarrow H+OH*$. Experiments have captured the resulting $OH*$, but other reactive oxygen species may also be produced.

The disclosure restricts the laser regime such that the treatment is always below the optical breakdown, and thus relies on the ionization potential for alteration of corneal geometry or the generation of cross-links in other tissue, such as cartilage. If a femtosecond laser operates below the energy level required for optical breakdown, ionization of atoms within the focal volume is possible. The ionization probability has a number of resonance maxima due to intermediate transition of the atom to an excited state. In the vicinity of such maximum the ionization cross-section increases by several orders of magnitude enabling ionization even if the frequency of the incoming electromagnetic wave is lower than the ionization potential. Tests (including spin trapping characterization) confirm that such a scenario enables creation of singlet oxygens, which likely react with the free carbonyl groups in the collagen chains. Such reactions result in crosslink formation. In a particular test, dityrosine crosslink was formed after femtosecond oscillator treatment of L-tyrosine solution.

The methods and systems can be used to treat various corneal disorders including keratoconus, myopia, hyperopia, stigmatism, irregular astigmatism, and other ectatic diseases (e.g., those that result from a weakened corneal stroma). The methods and systems can also be used in refractive surgery, e.g., to modify corneal curvature or correct irregular surfaces and higher order optical aberrations. The methods and systems can also be used to induce cross-linking in cartilage for treatment of osteoarthritis or other connective tissue disorders.

As embodied herein, ionization can be created within tissue using a laser emission that is absorbed by the tissue. For example, the laser emission can be based on ultrashort laser pulses. As used herein, the phrase "ultrashort laser pulses" includes emissions in the femtosecond, picosecond, and nanosecond ranges. Nonlinear absorption of laser emissions can occur in part due to the highly compressed nature of the light pulses, allowing treatments of the interior of a transparent dielectric, such as corneal tissue, without affecting the surface layer.

The ultrashort laser pulse can induce low-density plasma that ionizes water molecules within the tissue, but the laser operates below the energy level required for optical breakdown. Optical breakdown is the effect of an ultrafast laser focused in the interior of collagen rich tissue, where photoionization triggers non-linear absorption. Continued supply of incoming photons leads to the buildup of free electrons, further leading to avalanche ionization, which enhances the growth of free electron density resulting in formation of plasma. As contrasted from the low-density plasma, high-density, opaque plasma strongly absorbs laser energy through free carrier absorption. The high-density plasma expands rapidly, creating a shock-wave which propagates into surrounding material, creating optical breakdown.

Collagen cross-linking can be safely induced when the laser is operated below optical breakdown level in the so-called "low-density plasma" regime. For example, the laser emission, as defined by its wavelength, temporal pulse width, and pulse energy, as well as the numerical aperture of the scanning objective and the scanning speed should be high enough to induce ionization of water molecules in the collagen rich tissue, but below optical breakdown level. Further, such ionization can be induced in the cornea without reducing the transparency of the cornea.

Various parameters of the laser can be manipulated to control the safety and efficiency of the cross-linking of the collagen. For example, the laser beam, as defined by its wavelength, temporal pulse width, and pulse energy, as well as the numerical aperture of the scanning objective and the scanning speed should be high enough to induce ionization of water molecules in the cornea, but below optical breakdown level. Accordingly, these parameters can be maintained within certain ranges.

Figure 6:
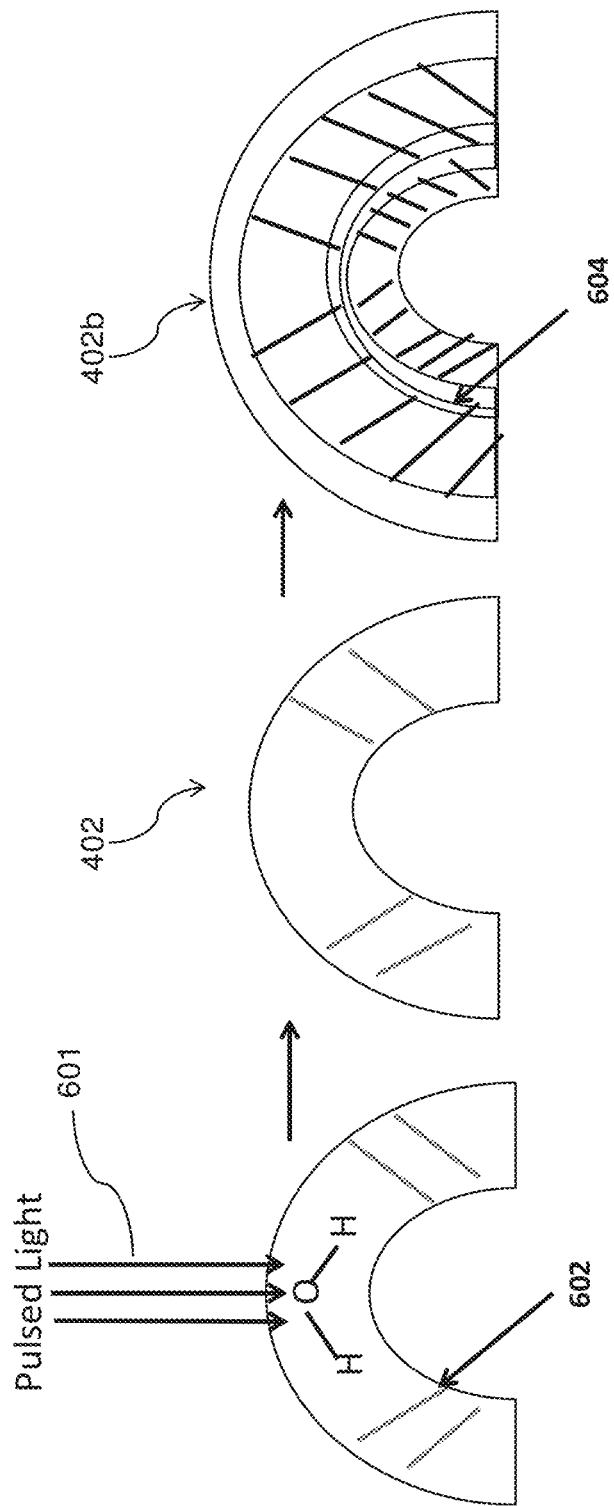
FIG. 6 illustrates a possible cross-linking mechanism for reshaping cornea using a laser.

Without being bound to a particular theory, the ionization can cause the formation of reactive oxygen products, such as singlet oxygen, $OH^-$, and $H_2O_2$, which in turn can interact with collagen and increase cross-linking in the fibrils, as shown in FIG. 6. Additionally, singlet oxygen generated by the ionization can inactivate collagenase and have a germicidal effect, increasing the utility of these methods for clinical applications. In embodiments, deuterium oxide can be introduced onto the cornea to prolong half-life of the produced singlet oxygen, thereby increasing cross-linking efficiency.

In certain aspects, the presently disclosed subject matter provides methods of inducing such ionization. The methods can be used in the treatment of various ectatic diseases or during refractive surgery. The methods can include modifying the corneal curvature by inducing selective corneal cross-linking.

Corneal deformations can be induced using a laser emission, as described in further detail below. Corneal deformations can be selectively induced using a patterned laser exposure. The pattern of exposure can depend on the desired deformations, and can be customized to the patient. In embodiments, the method can include mapping the topography of the patient's eye prior to treatment and designing a pattern of exposure based on that topography.

Figure 2:
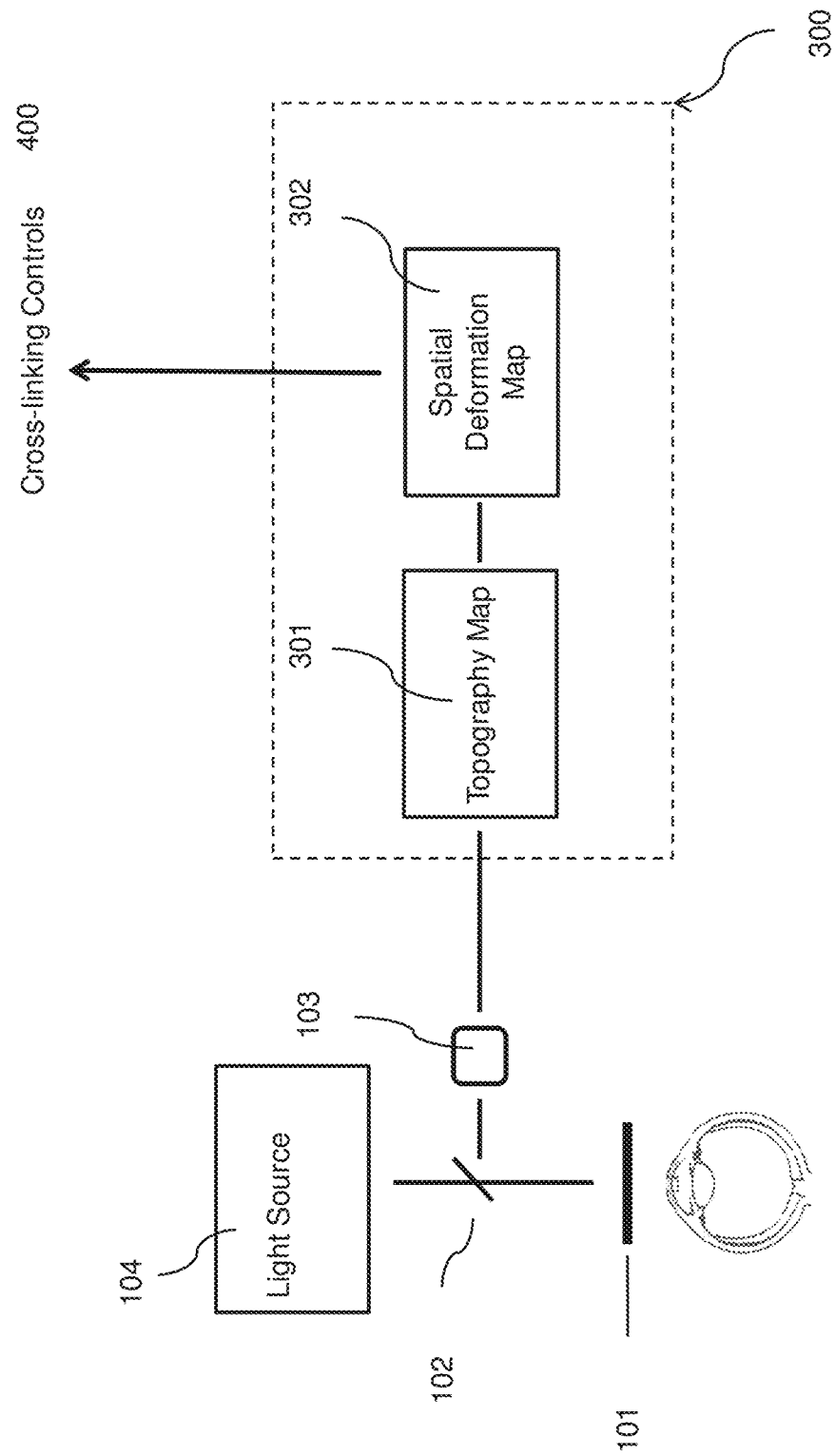
FIG. 2 illustrates a diagram of exemplary topography controls.

For the purpose of illustration and not limitation, FIG. 1 is a schematic representation of an exemplary system according to a non-limiting embodiment of the disclosed subject matter having two subsystems: a Topography System 100 and a Cross-linking System 200. For the purpose of illustration and not limitation, FIG. 2 is a further schematic representation of the Topography System 100.

As shown in FIG. 1, an embodiment of the cross-linking system 200 includes an objective 201. The objective 201 can be a scanning objective with a large numerical aperture. The large numerical aperture allows the objective 201 to focus diffuse light to a small area. A laser 203 supplies the light (laser light) to the objective 201. In an embodiment, one or more optical filters 202 may be interspersed between the laser 203 and the objective 201. The laser 203 can be a femtosecond laser that outputs laser light. In some embodiments, the laser light has a single frequency, and in other embodiments includes multiple frequencies. Embodiments may use any wavelength including multiple or continuous spectra covering a wide range of wavelengths. However in embodiments, preferably radiation at frequencies that may harm tissue or reduce the locality of the generation of reactive species are minimized or eliminated. Radiation that may be directly absorbed by the collagen may be minimized or eliminated. In an embodiment the frequency or frequencies of the laser 203 are outside of the ultraviolet range. In embodiments, the frequency or frequencies of the laser 203 are in the infra-red frequency band. The laser 203 receives control input from controls 400, which may be implemented on a stand-alone processing device or as embedded circuitry of the system.

Figure 4:
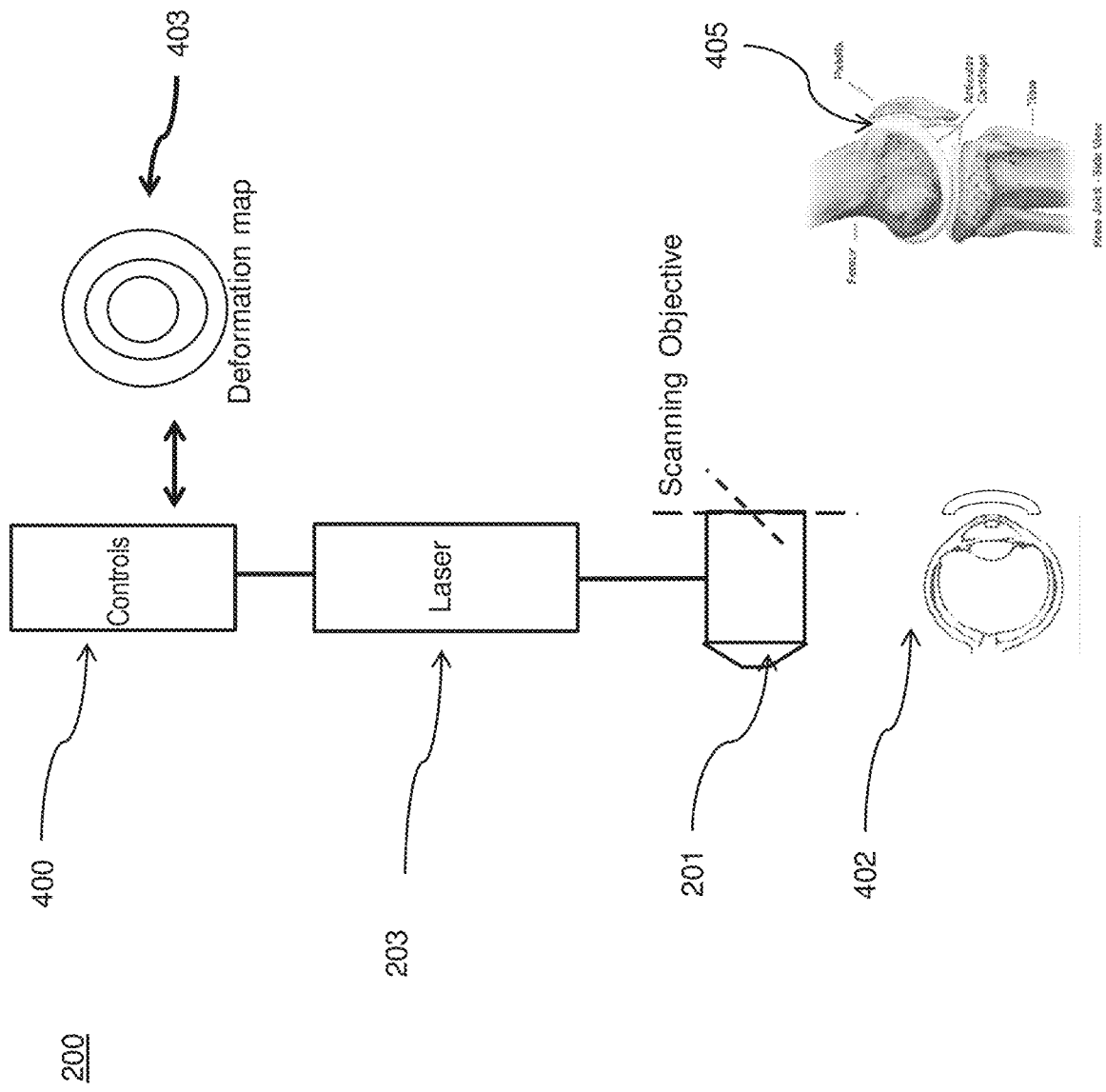
FIG. 4 illustrates a diagram of an exemplary cross-linking system.

As further shown in FIG. 1, the objective 201 focuses incoming laser light into a focused beam 601 which irradiates a target. In the example of FIG. 1, the target is tissue 411. In embodiments, the tissue 411 could be a cornea 402, cartilage 405, or other tissue. FIG. 4. illustrates embodiments with cornea 402 and cartilage 405. The objective 201 may have a large numerical aperture. In an embodiment, the numerical aperture is 0.6, with a long working distance.

Referring still to FIG. 1, a topography system 100 includes controls 300 which communicate with controls 400 of the cross-linking system 200. The topography system 100 includes a light source 104 and an imaging device, such as a camera 103. The light source 104 projects light to mirror 102 and a device, such as a mask, to produce an illumination pattern 101. The illumination pattern 101 guides the cross-linking system 200 to induce cross-linking in specified locations to produce the desired change in the treated tissue.

Referring to FIG. 2, additional details of the controls 300 of the topography system 100 are shown. A spatial deformation map 302 defines spatially the deformation of the cornea, which, when considered with the topography map 301 of the cornea, provides information on where to induce cross-linking.

Figure 3:
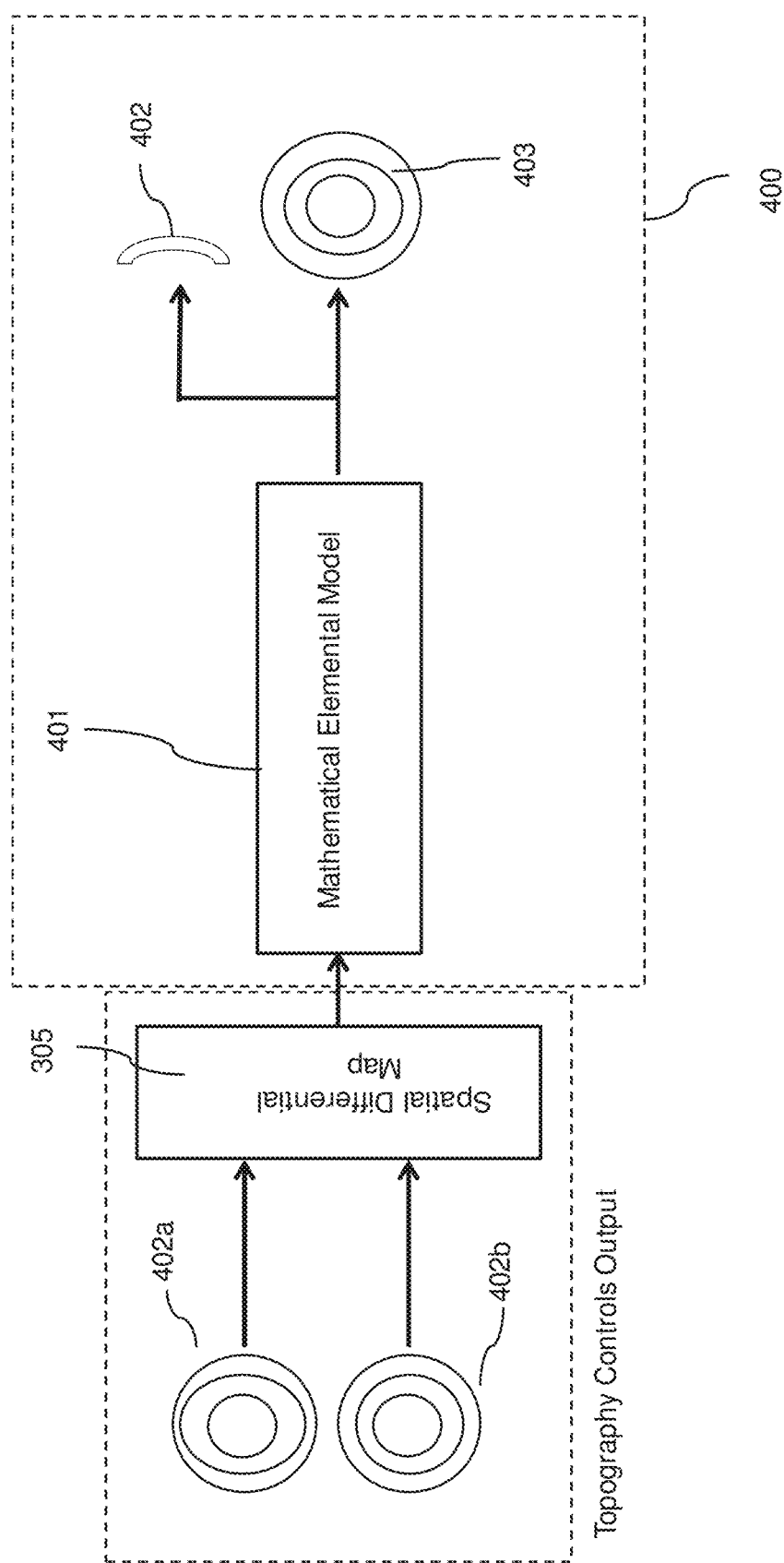
FIG. 3 illustrates a diagram of exemplary cross-linking controls.

Referring to FIG. 3, a skilled artisan will understand how to create a topographical map 301 of the cornea. By comparing the topographical map of the patient's cornea to a desired corneal topography, the control system 300 then generates a spatial differential map 305. As shown in FIG. 3, a mathematical elemental model 401 may be used to compare existing corneal topography to desired corneal topography to define a deformation map 403.

In embodiments, the illuminated pattern 101 can be a series of concentric rings. In embodiments, the control system 300 can be a processer coupled to a memory and further coupled to a storage device.

As embodied herein, a laser can induce ionization to cause corneal cross-linking. For the purpose of illustration and not limitation, FIG. 4 is a further schematic representation of a non-limiting embodiment of a system in accordance with the disclosed subject matter. In embodiments, the control system 400 is linked to a laser 203 and further linked to one or more scanning objectives 201. In case of multiple scanning objectives 201, the set of scanning objectives 201 can enable the laser 203 to raster a pulsed beam across predetermined regions of the patient's cornea through the coupling device. The regions of the patient's cornea to be scanned in raster fashion can be related to the deformation map 302 generated by the control system 400, or another pattern of exposure designed for the treatment. The cross-linking caused by the ionization induced by the laser can create corneal stiffening that alters the dimensions of corneal curvature in a predictable way.

Referring again to FIG. 4, the scanning objective 201 can be also focused on cartilage 405 to induce cross-linking in such tissue. In this example, the deformation map 403 of a cornea would not be used, but instead a different pattern would be used to illuminate the cartilage 405. While not illustrated in FIG. 4, in certain embodiments the scanning objective 201 may be replaced or supplemented with an optical pathway to guide the laser light to the treatment tissue. In an embodiment, the optical pathway may be an endoscope that is used to guide the laser light to cartilage in a live patient In embodiments, the cornea can be scanned in raster fashion with the laser beam in multiple layers. For example, the laser beam can scan the cornea 402 in a first pattern of exposure, and then scan the cornea in a second pattern of exposure. The first pattern of exposure and the second pattern of exposure can wholly or partially overlap on the cornea to provide multiple layers of exposure. Using a high-aperture canning objective 201 enables the application of energy at different specified depths in the cornea 402.

Figure 5A:
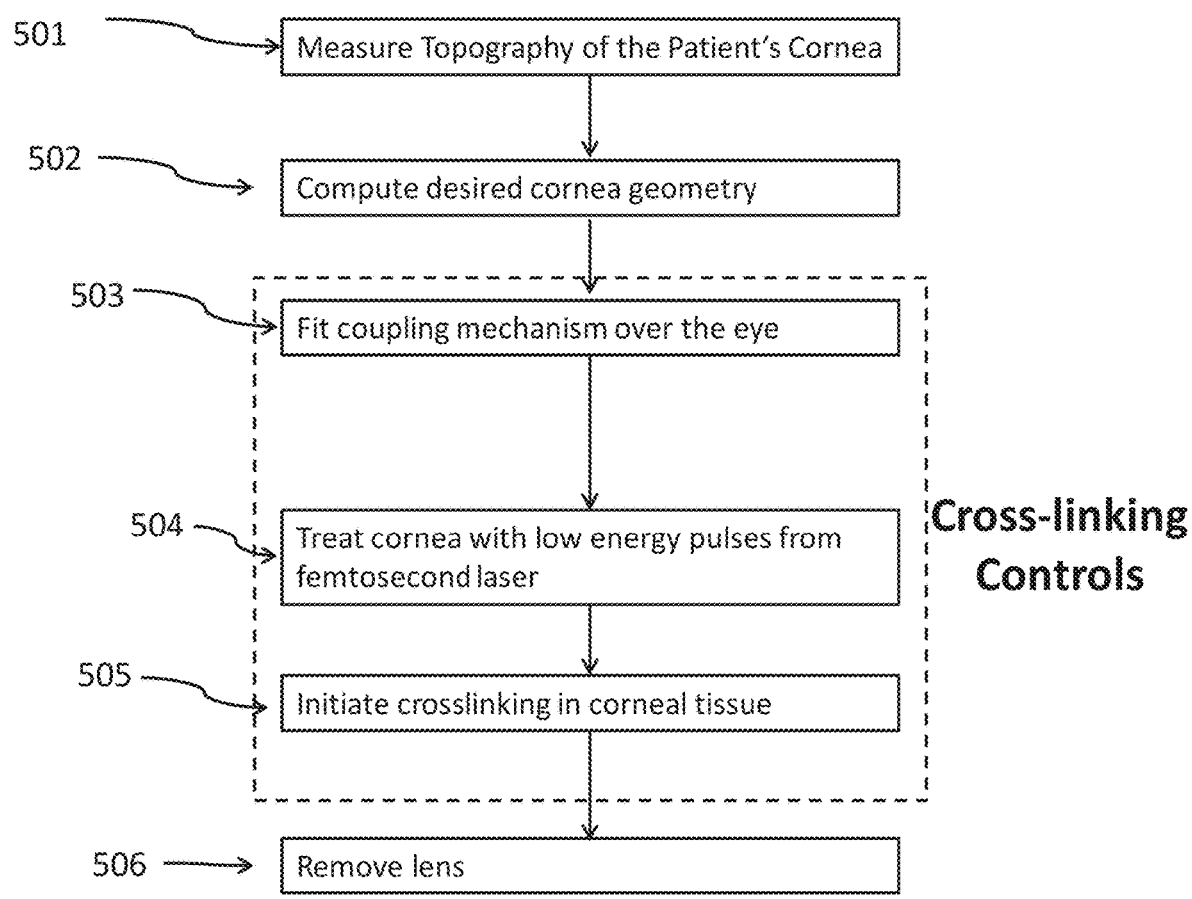
FIG. 5A illustrates a flow diagram of an exemplary cross-linking process applied to the cornea.

Referring to FIG. 5A, an example of a method of inducing cross-linking in corneal tissue is shown. In step 501, the topography of the patient's cornea is measured. In step 502, the desired cornea geometry is computed. In some embodiments, the goal may to strengthen the cornea without changing its shape. In this case, step 502 computes the desired locations to strengthen without changing the corneal shape. In an embodiment, a coupling mechanism may be placed over the eye to be treated in step 503. However, this method is not limited to such embodiments, and the cornea may be treated without a coupling mechanism also. In step 504, the laser 203 is driven to emit low energy pulses which are guided and focused by the cross-linking system 200 discussed above. As shown in step 505, the interaction of the pulse laser with the treated tissue and/or the aqueous medium in and around the tissue initiates cross-linking. In step 506, a lens of the coupling mechanism (if one was used) is removed from the cornea.

In embodiments, the techniques of the present disclosure can be used to modify corneal curvature. For example, these techniques can be used in corneal flattening, i.e., to reduce the optical power of the corneal surface. In embodiments, the cornea 402 can be flattened by controlling the spacing and layering of laser pulses within a central treatment zone. For further example, these techniques can be used in corneal steepening. By way of example, and not limitation, the pattern can include one or more circles, ellipses, annuli, and combinations thereof, which can be chosen based on the desired shape change. For example, a circular treatment pattern can be employed to flatten the curvature of the cornea. An annular (e.g., toric) treatment pattern can be employed to steepen the curvature of the cornea. Additionally, the density of the treatment (i.e., the points of exposure) can be modulated.

Moreover, certain patterns of exposure can be used to treat certain disorders. For example, an elliptical shape, which can be disk-shaped or toric, can be used to treat astigmatism. The elliptical pattern can be designed such that one meridian of the astigmatism is flattened more than the other. During treatment, the elliptical pattern can be placed over the corneal projection of the entrance pupil and aligned such that the astigmatic axis of the pattern overlies the astigmatic pattern on the cornea. As such, the steeper axis of the astigmatism can be flattened more than the flatter axis to correct the astigmatism.

Additionally, the pattern of exposure can be used to treat corneal infections and melts. The ionization induced by the pattern of exposure may be employed to kill bacteria, fungi, and infected cells. For example, first, the extent of the infection and/or melt can be determined using various methods as known in the art, including slit lamp bio microscopy, fluorescein staining, optical coherence tomography (OCT) analysis of the corneal structure, and other conventional clinical techniques. Then, the corneal tissue can be treated in multiple layers to cover the volume of damaged stroma and/or infectious elements.

In addition to the shapes previously described, the pattern of exposure can further include additional shapes including bow-ties and concentric rings. Additionally, or alternatively, the pattern can include a custom-designed shape. For example, in embodiments, a custom-design shape can be designed to correct a higher order aberration. In embodiments, a custom-designed shape can be based on the cornea topography. In particular embodiments, for example, where the patient has an uneven corneal topography, a custom-designed shape may be preferred.

Thus, as embodied herein, it is not necessary to provide a physical device to mechanically induce the deformations prior treating the cornea with the laser emission. However, in embodiments, a physical device, such as a suction contact lens, can be used to induce corneal deformations in conjunction with laser beam treatment. The device can be customized such that the back of the device forms a mold for the desired deformations, i.e., based on the deformation map 302.

FIG. 6 illustrates conceptually the change in corneal shape after the cornea is exposed to focused beam 601 of pulsed laser light. Collagen 602 is naturally present in the cornea. The application of focused beam 601 results in the production of free radicals from water in the treatment area, without causing optical breakdown in the corneal tissue. The free radicals induce cross-linking, shown conceptually as cross-links 604 in the reshaped cornea 402*b*. The induced cross-links can change the shape as well as the elasticity of the cornea (e.g., to counteract keratoconus.)

Figure 5B:
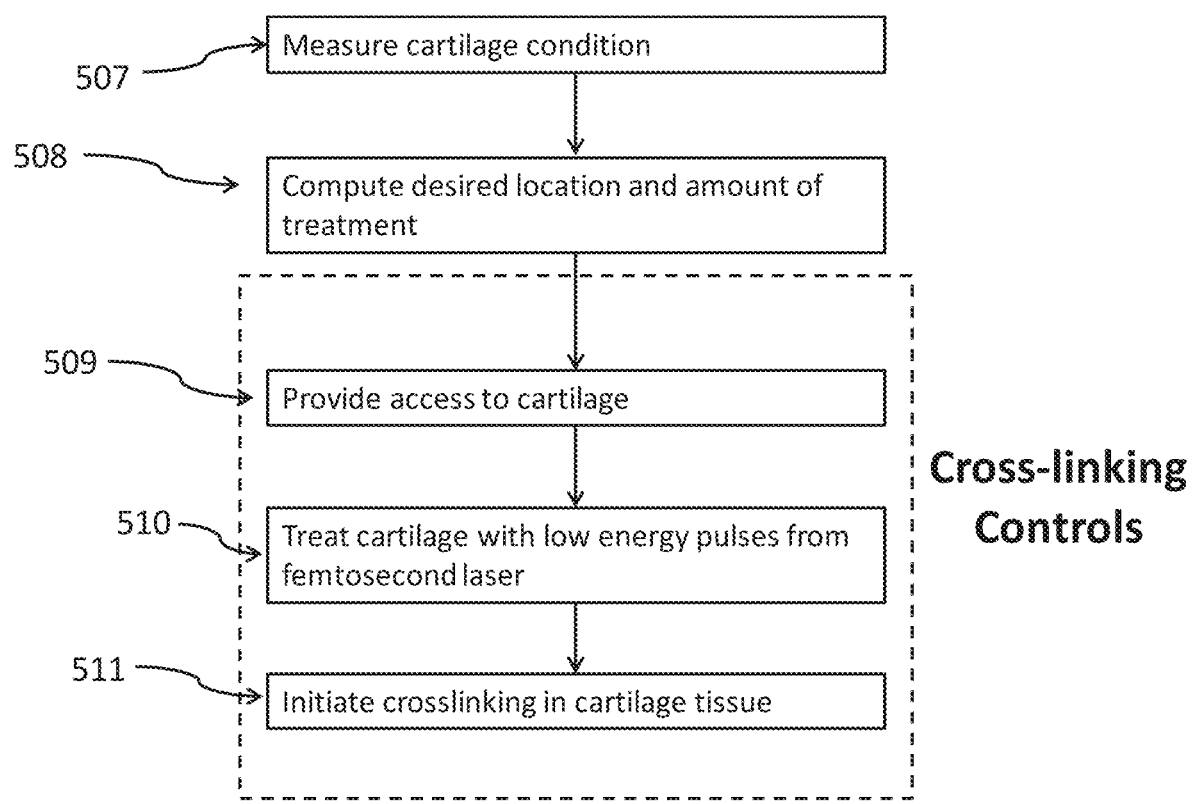
FIG. 5B illustrates a flow diagram of another exemplary cross-linking process applied to cartilage.

Referring to FIG. 5B, an example of the process of inducing cross-linking in cartilage is illustrated. This process has some similarities with that shown in FIG. 5A. In step 507 the cartilage is assessed to determine its condition. In step 508, the desired location(s) and amount of treatment is computed. The treatment can be spread out over a large area or focused on only specific areas. The treatment can be varied by controlling the power and pulse rate of the laser 203. In step 509 access is provided to the cartilage to be treated. In an embodiment, this may be through surgical incisions to provide access to an endoscope. An endoscope may guide the pulsed laser light through an optical pathway to the target area. In step 510 low energy pulses from a femtosecond laser are applied to the desired treatment location(s), with the scanning objective 201 possibly moving or scanning over the treatment area. In step 511, cross-linking is initiated in the cartilage tissue in response to the laser treatment.

In embodiments described previously, the laser can emit ultrashort light pulses, e.g., with a temporal length below 1 nanosecond. Generation of such short pulses can be achieved with the technique of passive mode locking. The laser 203 can be any suitable laser type, including bulk lasers, fiber lasers, dye lasers, semiconductor lasers, and other types of lasers. In an embodiment, the laser operates in the infrared frequency range. In other embodiments, the lasers may cover a wide range of spectra domain. In embodiments, the disclosed subject matter can be implemented as an add-on system to a femtosecond laser system, such as used in certain Lasik systems.

As embodied herein, the operating parameters of the laser can be varied depending on certain environmental factors. By way of example, and not limitation, such environmental factors can include the nature of the interstitial fluid, the presence and amounts of dissolved nutrients, the osmolarity, the humidity, and the oxygen levels. For example, certain environmental factors can impact, e.g., the thickness of the cornea or treatment efficiency. Thus, in embodiments, the operating parameters and/or pattern of exposure can be modulated accordingly.

In embodiments, and with further reference to FIGS. 1 and 4, the scanning objective(s) 201 can include a high magnification, e.g. 40×, objective lens and a galvanometer for scanning the laser across the cornea. The objective lens 201 can have a high numerical aperture, e.g., 0.6, with a long working distance. The objective can be interchangeable to accommodate for use of a range of numerical apertures as well as working distances.

In embodiments, the scanning objectives can include multiple mirrors on an automated track, as illustrated in FIG. 7C. For the purpose of illustration and not limitation, FIG. 7C is an exemplary schematic representation of the scanning objectives. The laser light can be directed along the x axis. Mirror A (702) can travel along x-axis track. At a determined x position, mirror A can deflect the incoming laser light orthogonally into they plane. Mirror B (704) can be adjusted such that its x position is the same as that of mirror A. Mirror B can then traverse along they axis to a desired y position to deflect the laser light orthogonally into the z plane towards the objective lens. The objective lens and mirror B can be housed on the same posting and move together. Traversing the track can be done continuously or discretely through DC servo motor control along the rails. The scanning of the cornea with the laser beam can be accomplished by moving the mirrors, according to the control system 400 The mirrors and lens are constructed with wavelength and energy appropriate materials known in the art.

In particular embodiments, the laser can be a Nd:Glass femtosecond laser. In embodiments, the laser wavelength can be in the range from about 250 nm to about 1600 nm. In embodiments, the femtosecond laser can have a temporal pulse width of from about 20 fs to about 26 ps. In embodiments, the pulse energy is from about 0.1 nJ to 100 nJ, 0.1 nJ to about 50 µJ, 0.1 nJ to about 10 µJ, from about 0.5 nJ to 50 nJ, or from about 1 nJ to 10 nJ. In embodiments, the femtosecond laser can be a Spirit femtosecond laser in combination with a Spirit-NOPA™ amplifier (Spectra-Physics, Santa Clara, Calif.). The numerical aperture of the scanning objective can range from about 0.05 to about 1. In embodiments, the numerical aperture can be selected based on the pulse energy, e.g., by balancing the numerical aperture and the pulse energy. The laser beam can be stationary or moving. Where the laser beam is moving, the scanning speed can be any suitable scanning speed based on the equipment being used.

As embodied herein, the laser can provide one or more beams. Thus, the presently disclosed techniques can be used to provide a multiple beam exposure. Multiple beam exposure can increase the treatment area and/or decrease the length of exposure. For example, treatment with multiple beams can decrease the exposure time to less than an hour. In embodiments, treatment with multiple beams can decrease the exposure time to less than 5 minutes per layer, e.g., 2 to 3 minutes per layer.

Figure 7A:
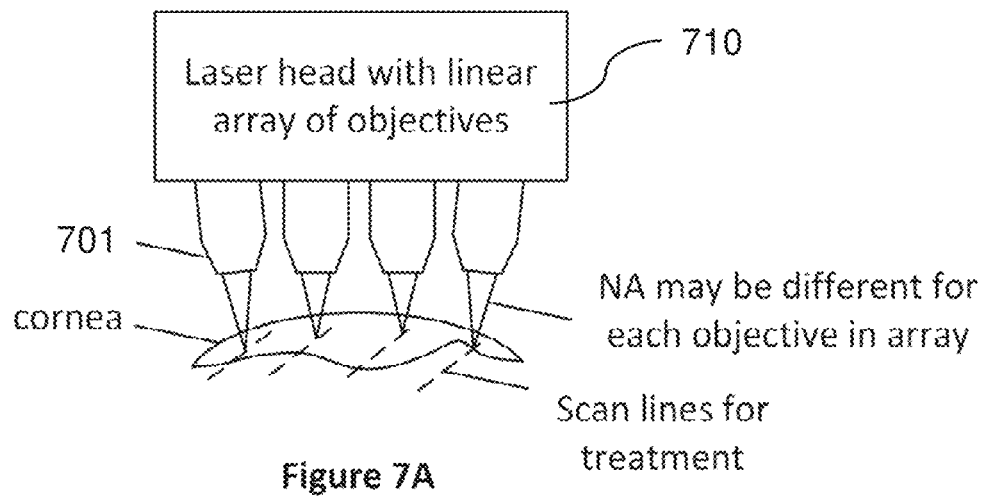
FIG. 7A illustrates a diagram an exemplary system for providing multiple beam exposure.
Figure 7B:
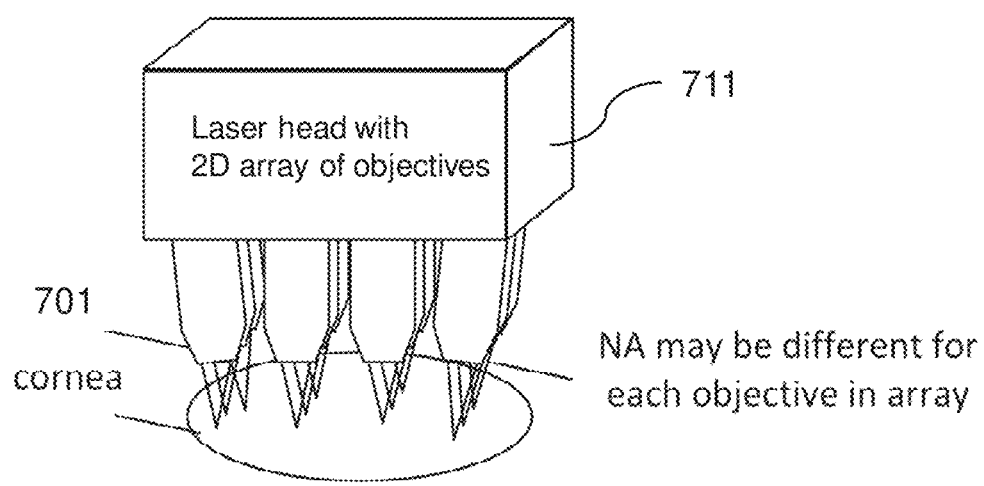
FIG. 7B illustrates a diagram another exemplary system for providing multiple beam exposure.

In embodiments, the multiple beams can be provided by splitting a laser beam to multiple scanning objectives. For example, a laser head can include multiple scanning objectives bundled together, as shown in FIGS. 7A and 7B. FIG. 7A illustrates an example of a linear array 710 of objectives 701. FIG. 7B illustrates a two dimensional array 711 of objectives 701. Although the objectives 701 are illustrated as identical in the drawings, in embodiments different objectives are used at different positions in the array. A high energy laser beam (e.g., having a pulse energy of greater than about 10 µJ) can be split using a beam splitter to send individual laser beams to each scanning objective. Therefore, the number of passes required to fully treat the cornea can be reduced by providing multiple laser beams simultaneously. In embodiments, an entire corneal layer could be treated simultaneously, e.g., by bundling many scanning objectives to the laser head such that only one pass is required.

The following examples are merely illustrative of the presently disclosed subject matter and should not be considered as limiting in any way.

Example 1: Use of Femtosecond Laser to Cross-Link Porcine Cornea

This Example illustrates the effect of femtosecond laser irradiation to a porcine cornea.

Porcine eyes were obtained from a commercial supplier (Animal Technologies, Tyler, Tex.). The eyes were harvested and frozen within 3 hours after slaughter. The eyes were carefully thawed immediately before the example was performed. The globe was mounted onto the metal ring and fixed with cyanoacrylate, such that the cornea was placed at the center and left exposed after the mounting excess tissue was removed. Subsequently, the upper surface of cornea was moistened with phosphate buffered saline (PBS) solution and a coverslip was placed on top of the specimen to reduce light scattering from the laser. Placement of the coverslip also ensured the flatness of the top surface of the cornea. The metal ring with cornea was fixed onto a 3-axis motorized translation stage using a custom made holder.

Figure 8:
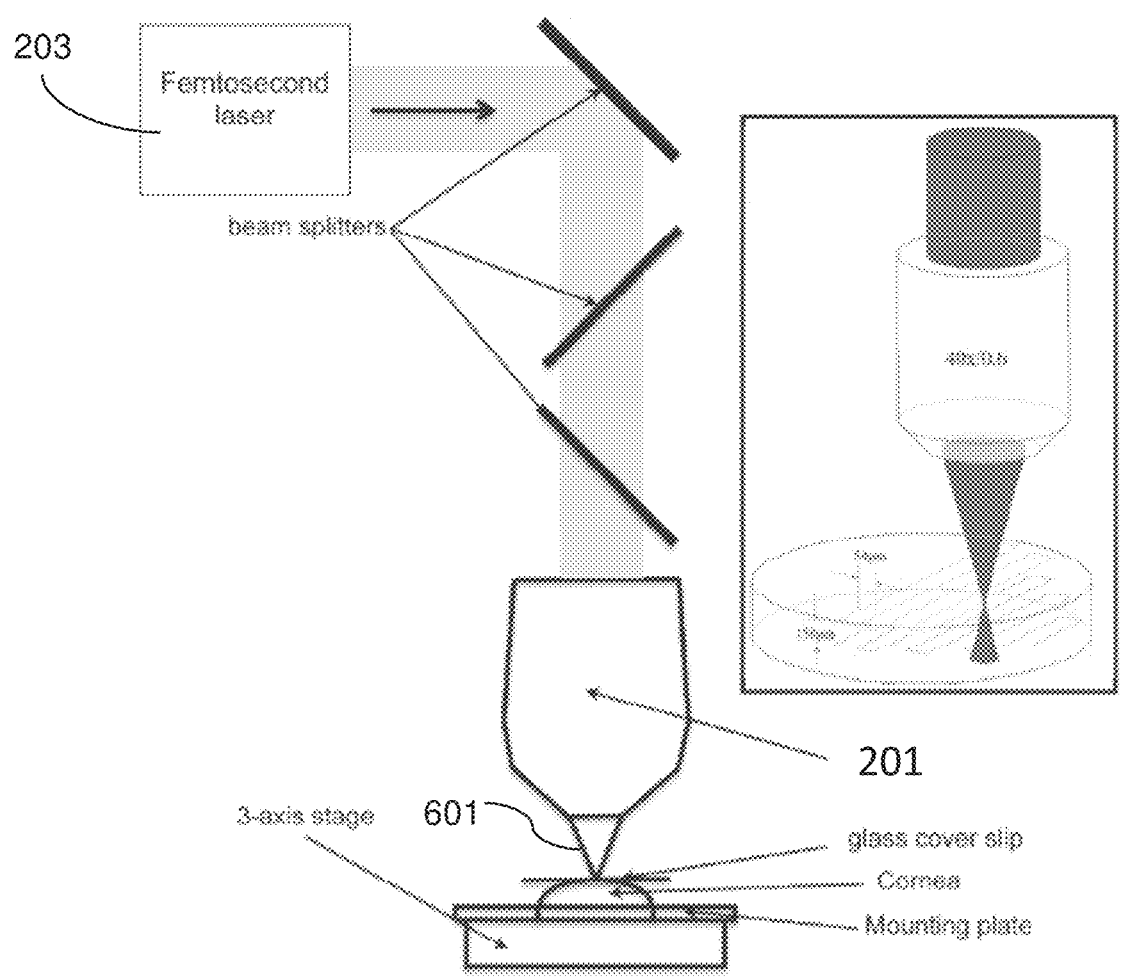
FIG. 8 illustrates an exemplary setup for Example 1 described below.

A Nd:Glass femtosecond laser system was used to generate laser pulses with temporal pulse width of 99 fs and 52.06 MHz repetition rate at 1059.2 nm wavelength. A Zeiss Plan Neofluar 40×/0.6 objective lens was employed to focus the beam, and the pulse energy was measured to be 60 mW after the objective lens. The laser beam was focused in the interior of cornea, creating planar zigzag patterns with 50 µm pitch at feed rate of 1 mm/s. Multiple planes parallel to the corneal surface were treated with 150 µm distance between two consecutive planes. During this process cornea was moistened with PBS solution to prevent drying. A schematic of the example setup is shown in FIG. 8.

Changes in the chemical composition of the corneas were assessed using Raman spectroscopy. Raman spectra were acquired with a confocal micro-spectrometer (Renishaw InVia), equipped with 1800 gr/mm. Incident laser excitation was provided by helium-neon laser with 632.8 nm wavelength, delivered by a 100× objective. Raman signal was acquired by 30 accumulations, each lasting 10 seconds.

Figure 9:
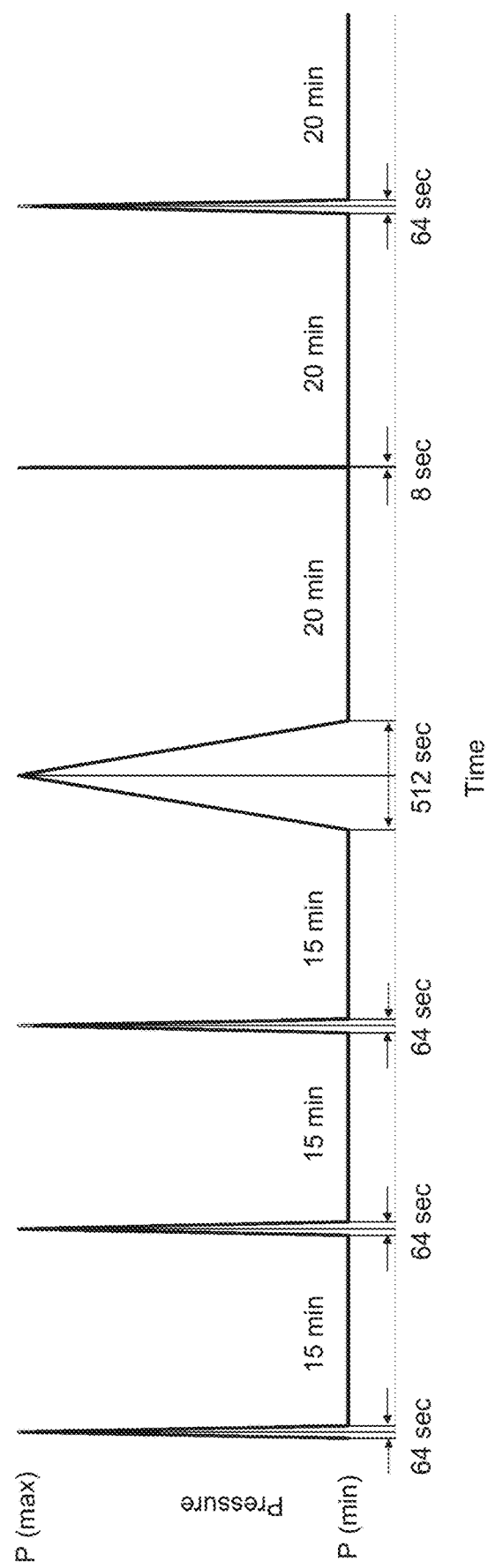
FIG. 9 demonstrates a schematic diagram of loading regime during the inflation test.

An inflation test was used to provide information about the changes in the mechanical properties of the corneas subjected to femtosecond laser pulses. A loading regimen consisting of a series of linear load/unload cycles was utilized on eight specimens to characterize the change in the mechanical properties of cornea subjected to femtosecond laser treatment. Each sample was initially subjected to two pressure linear load-unload cycles to determine the effects of pre-conditioning. These cycles were parted by a 15-minute recovery period. (FIG. 9). Pressure-displacement curves obtained from pre-conditioning were compared against one another and against the identical post-conditioning cycle to verify that the sample did not degrade during the test. Baseline pressure used was 0.5 kPa, the lowest pressure able to support the specimen without buckling. The maximum pressure used was 5.4 kPa. Pre-conditioning cycles were followed by three loading cycles, in which loading rate was varied. The first test had loading rate identical to the preconditioning, 0.15 kPa/s, and the latter two tests had loading rates of 0.019 kPa/s and 0.15 kPa/s, respectively.

Figures 10A, 10B:
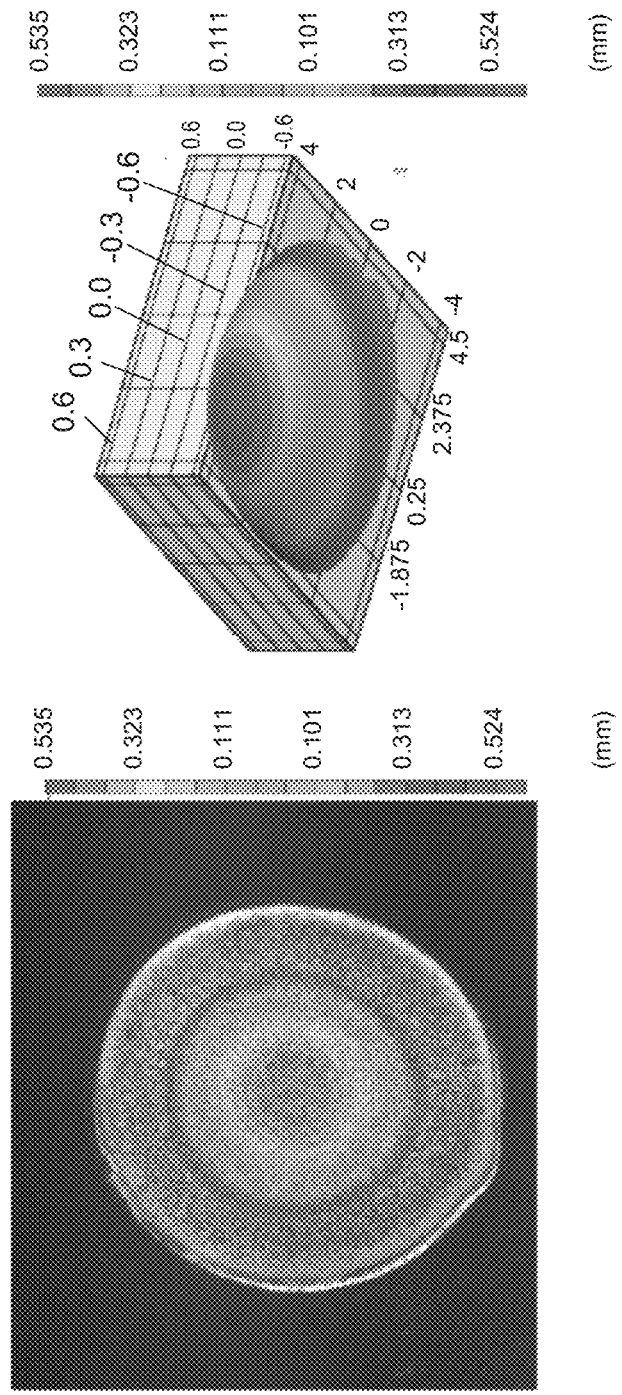
FIG. 10A demonstrates an initial shape of the cornea assessed by DIC.
FIG. 10B demonstrates an oblique reconstruction of the cornea by DIC.

Stereoscopic digital image correlation (DIC) system was employed to acquire spatially and time resolved displacement maps of the corneal surface during the inflation tests. Two cameras were located above the sample, at 15° angle with respect to the vertical axis. The image pairs were analyzed with 3D DIC software package (VIC 3D Correlated Solutions, Inc.). The reference configuration as a function of Z-heights for a matrix of x and y coordinates (FIG. 10), as well as deformation fields for each subsequent image-pair were extracted by the DIC algorithm. The algorithm was capable of providing displacement components U-, V-, and W-corresponding to the deformation along the x-, y-, and z-axes of the camera coordinate system. These axes were aligned with the optical axes of the cornea. For this example, only the deformation in the direction coincident with corneal bulging (W-displacement) was of interest. The nasal-temporal, the inferior-superior and the thickness at the center of each specimen were measured with caliper before and after the inflation test.

Figure 11:
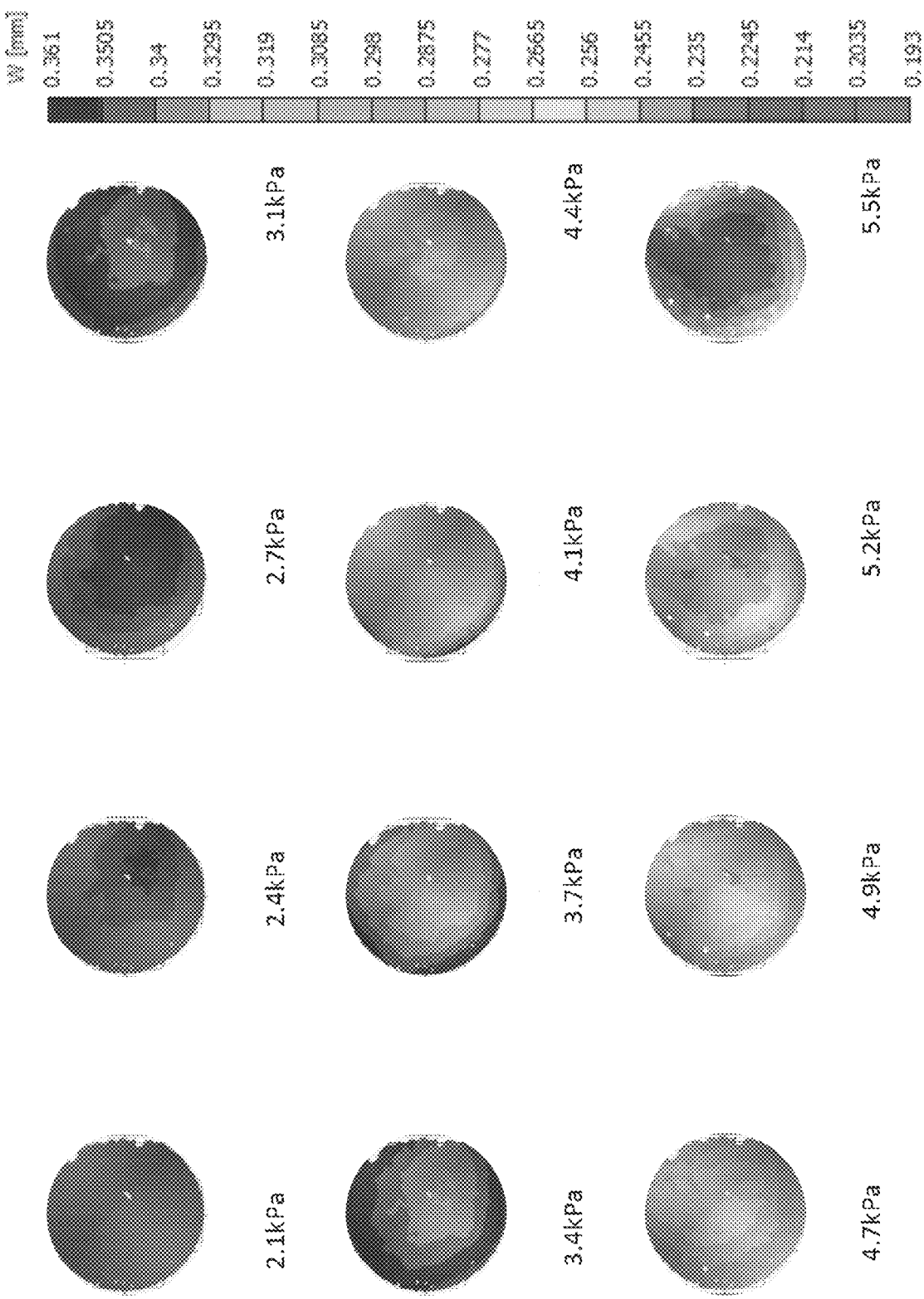
FIG. 11 demonstrates displacement maps of the control cornea in z direction at different pressures.

FIG. 11 shows examples deformation maps (such as a spatial deformation map 302) of porcine cornea at various pressures during the inflation test. Each image frame corresponds to one time step during the multi-cycle loading regimen. The deformation shown is along the z-axis, which coincides with the optic axis of the cornea. Specifically, the image frames shown correspond to the first loading regime and similar trends were observed when different loading rates were applied. Only one set of data is shown.

Figure 12:
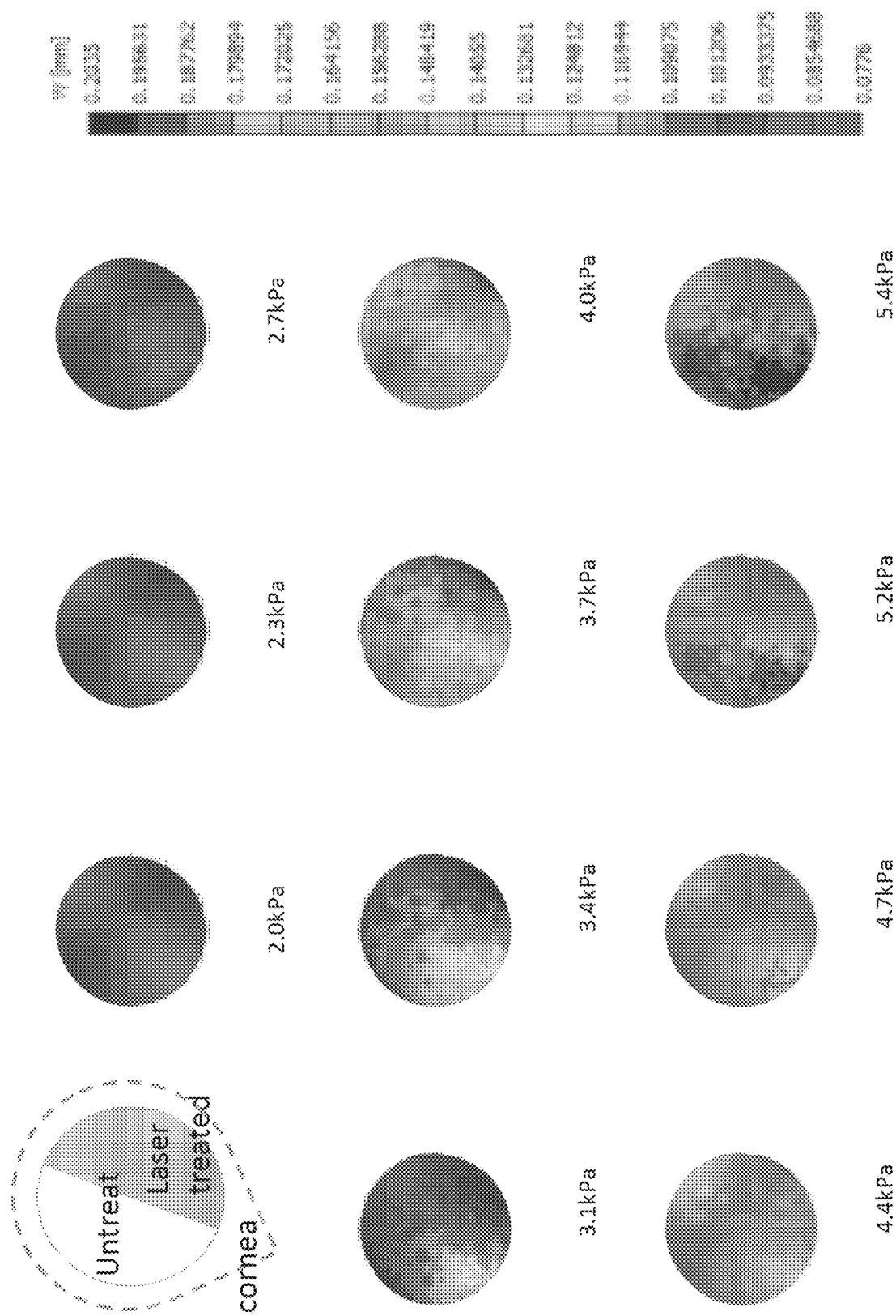
FIG. 12 demonstrates displacement maps of the half-treated cornea in z direction at different pressures.
Figure 13:
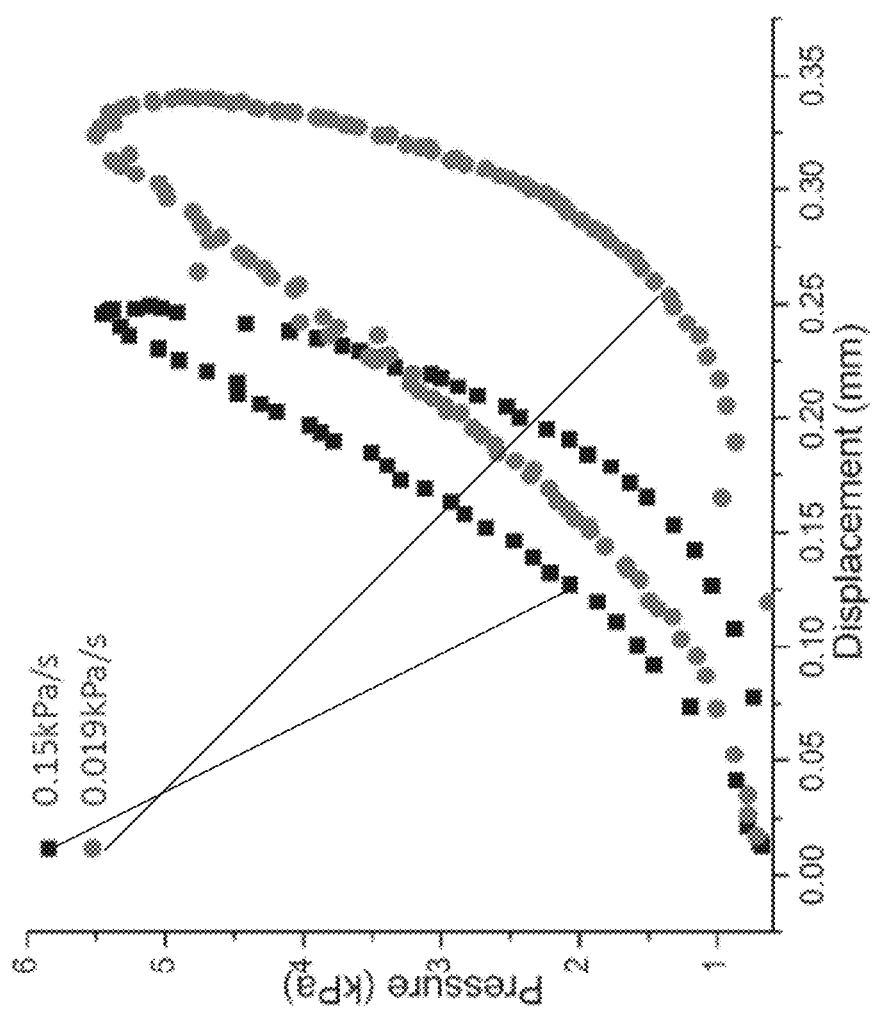
FIG. 13 demonstrates loading-displacement hysteresis curves for the control cornea.

While FIG. 11 shows data from the control cornea, FIG. 12 depicts the results of the corneal tissue, half of which was treated with the femtosecond laser. Nonzero values on the edges of DIC maps occur due to the condition of the DIC method to have a finite analysis window. Results shown correspond to the inflation regime characterized with 0.15 kPa/s rate. FIG. 11 also shows the deformation of the control cornea is axisymmetric. The apex displacement, defined as maximum out-of-plane displacement in the central part of the cornea, reaches value of 0.361 mm at 5.5 kPa pressure. The viscoelastic response of the cornea that resembles J-shaped pressure-displacement curve is observed. (FIG. 13). When the half-treated cornea is subjected to identical loading conditions, treated part of the corneal tissue exhibits less deformation than the untreated portion. The displacement in the entire cornea increases with the rise of the inflation pressure, but the deformation of the treated part of the corneal tissue is much lower than the untreated region. Maximum deformation in the untreated region is lower than the apex deformation in the control cornea.

The difference in the observed displacement between untreated and treated regions of the corneal tissue can be attributed to stiffening of the laser treated part of the cornea, which can be attributed to creation of cross-links that increase the structural stability of the stroma. The stiffened (i.e., treated) region required more pressure for displacement. The pressure-displacement curve was constructed by extracting the apex displacement at each time step of the inflation test (FIG. 13). For the control specimens, apex displacement was used, whereas in the case of half-treated sample, representative points in both treated and untreated region were utilized. Two different pressurization rates are compared.

Figure 14:
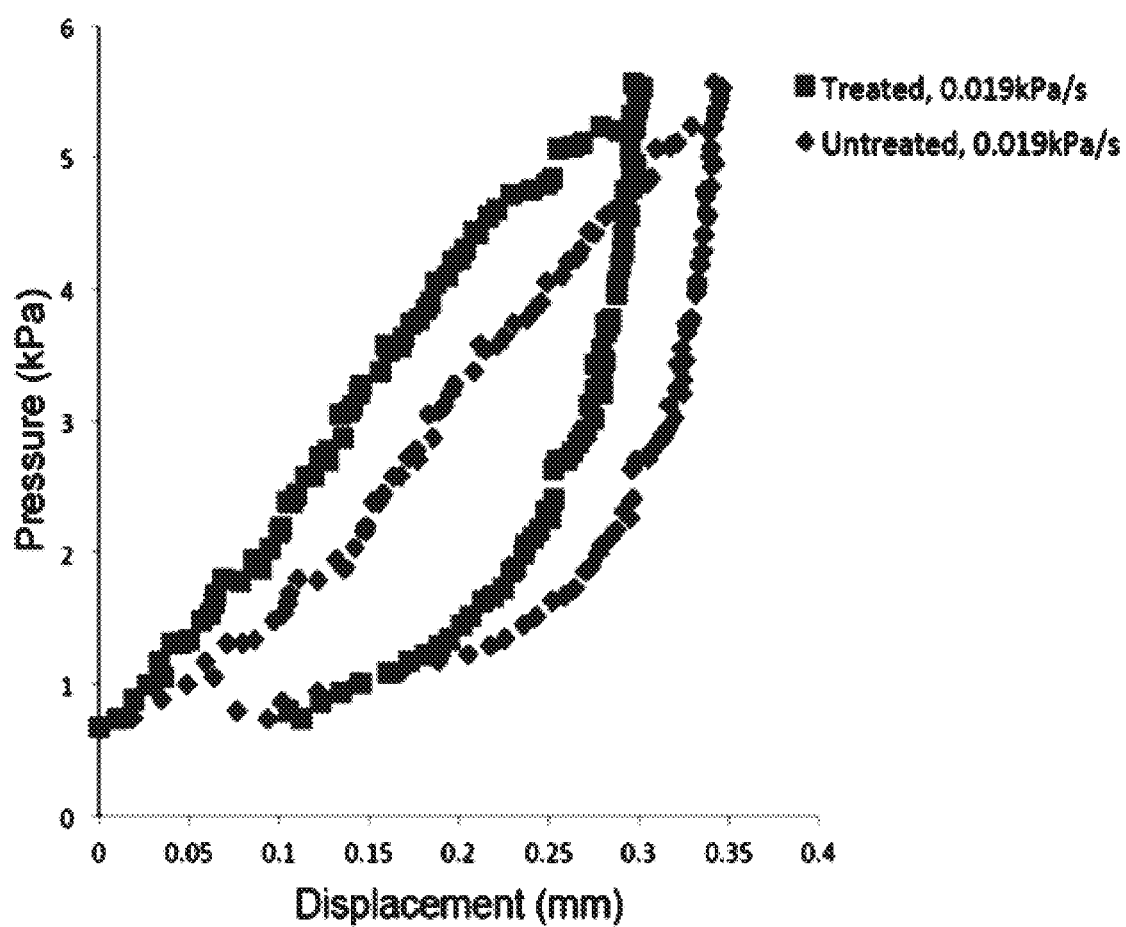
FIG. 14 demonstrates loading-displacement hysteresis curves for the half treated cornea and the control cornea at 0.019 kPa/s pressurization rate.
Figure 15:
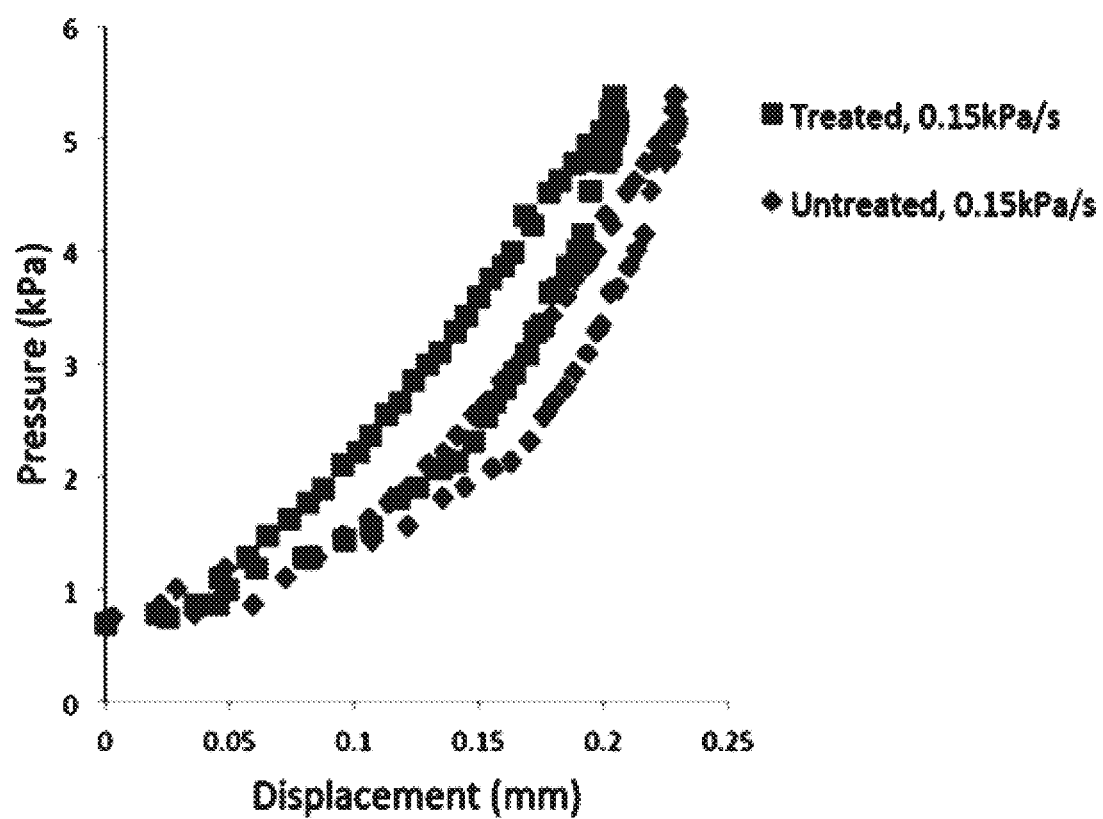
FIG. 15 demonstrates loading-displacement hysteresis curves for the half treated cornea and the control cornea at 0.15 kPa/s pressurization rate.

FIGS. 14 and 15 show hysteresis curves obtained from untreated and treated part of the porcine cornea, subject to 0.019 kPa/s and 0.15 kPa/s pressurization rates, respectively. The change in the relative slope of the hysteresis curve indicates stiffening of the corneal tissue, as more pressure was required to displace the treated tissue. The nonlinear ionization induced within the focal volume by femtosecond oscillator can create singlet oxygen, which then reacts with the free carbonyl groups subsequently forming the CXLs, which can be responsible for the observed corneal stiffening.

Figure 16:
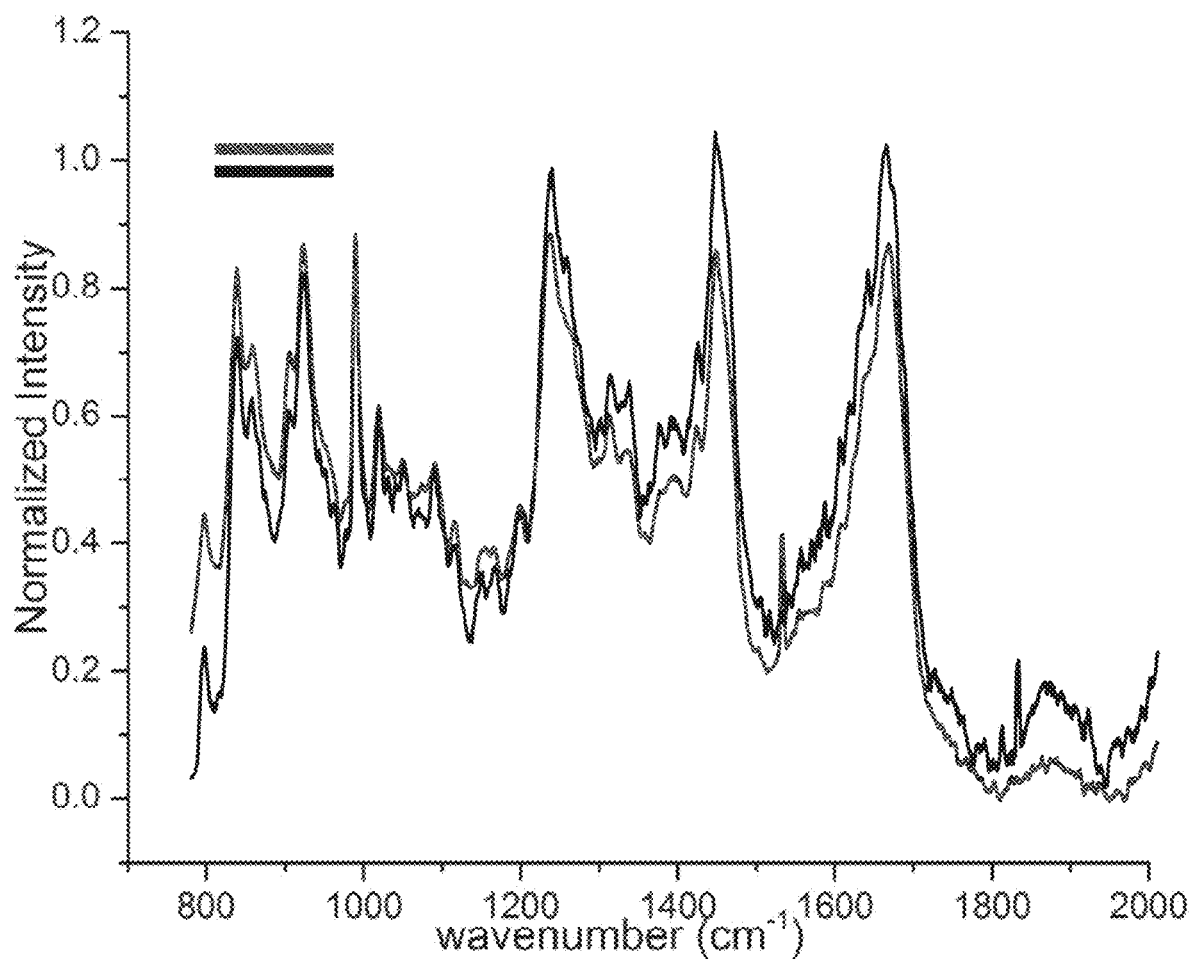
FIG. 16 shows Raman spectra of a treated and a control region of the half-treated cornea.

Raman spectra of the untreated and treated part of the cornea (FIG. 16) show difference in the chemical composition after laser irradiation. The Raman signal was normalized with respect to phenylalanine peak located at 1000 cm$^-$ The Raman band associated with carbonyl group (1670 cm$^{-1}$) and the peak associated with Amide III (1265 cm$^{-1}$) are diminished in the treated part of the cornea, which is consistent with cross-linking because the ionization results in the formation of singlet oxygen that can then react with free carbonyl groups to form the corneal cross-links.

Figure 17A:
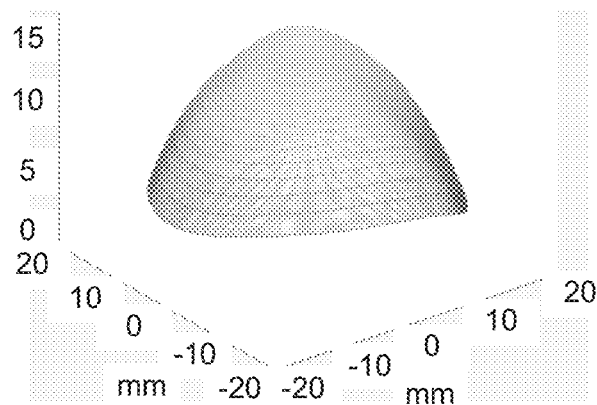
FIGS. 17A-17C illustrate the results of the disclosed method and system applied to porcine eye shape.
Figure 17B:
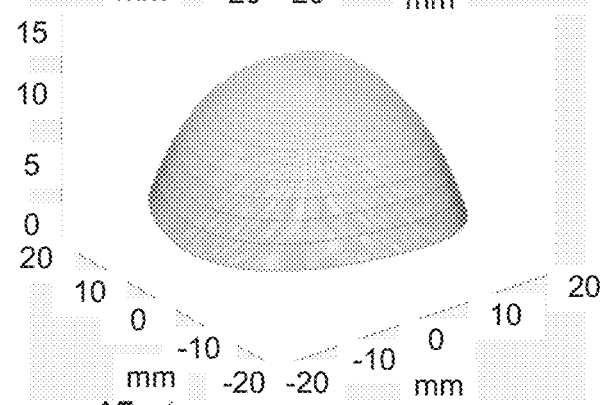
Figure 17C:
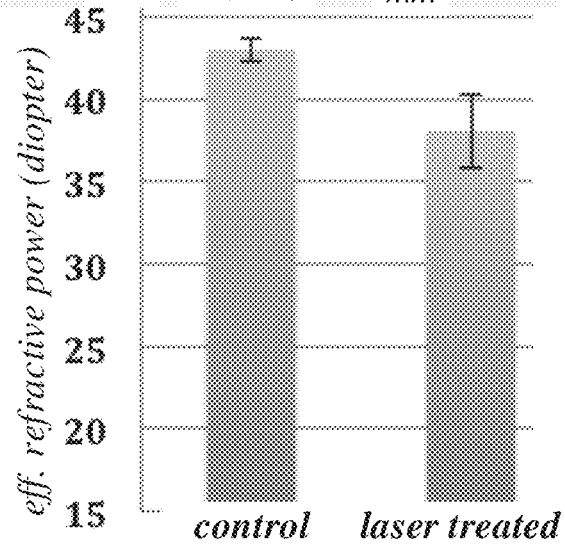

FIGS. 17A-C illustrate the results of the disclosed method and system applied to porcine eye shaped. FIG. 17A is an elevation map depicting topography of the cornea of a porcine eye before treatment, and FIG. 17B is an elevation map depicting topography of the cornea after treatment. The difference between the two can be more easily quantified by referring to FIG. 17C, which illustrates the difference in the effective refractive power of the two.

Electron Paramagnetic Resonance (EPR) Spectroscopy

Spin-trapping reagent 5,5-dimethy-1-pyrroline-N-oxide (DMPO, Cayman Chemicals, USA) was solved in Dulbecco's phosphate-buffered saline (DPBS), with final concentration of 100 mM, just before the treatment. 170 µL of the solution was placed into a shallow dish (2×8 mm) and put onto the 3-axis motorized stage for treatment. A control sample was concurrently prepared by following the same procedure. A Nd:Glass femtosecond laser system was used to generate laser pulses with temporal pulse width of 99 fs and 52.06 MHz repetition rate at 1059.2 nm wavelength. A Zeiss Plan Neofluar 40×/0.6 objective lens was employed to focus the beam, and the pulse energy was measured to be 60 mW after the objective lens. Immediately after the treatment the solution was collected into 0.5 mL tubes, which were then placed into liquid nitrogen canister and transported to EPR spectrometer (Bruker BioSpin GhbH EMX Electron Paramagnetic Resonance Spectrometer, Bruker BioSpin GmbH, Germany). Sample transport time between the treatment and EPR analysis never exceeded 15 minutes. The control samples were also collected into 0.5-ml tubes, transported in liquid nitrogen and characterized for comparison.

Temperature and Refractive Index Measurements

Porcine eyes were obtained from a commercial supplier (e.g., Animal Technologies, Tyler, Tex.). The eyes were harvested and flash frozen within 3 hours after slaughter. The eyes were carefully thawed immediately before the experiments. Corneas were harvested and mounted onto a custom built holder. After the mounting, excess tissue was removed and cornea placed onto the 3-axis motorized stage. Subsequently, cornea tissue was moistened with phosphate buffered saline (PBS) solution. The cornea was then punctured with needle-like head of a customized thermocouple (temperature measurement range 0-100° C.). The tip of the thermocouple was inserted in the middle of the harvested corneal tissue. Real-time temperature readings were displayed on a LED monitor. The above-described Nd:Glass femtosecond laser system was employed for the treatment. The focal point was aligned with the tip of the thermocouple and temperature distribution measured as the focal volume was circulated around the tip of the thermocouple. In addition to temperature measurements, potential refractive index changes in corneal refractive index were examined. In the central part of the cornea 3×5 mm rectangular area was treated following the same protocol. After the treatment, mounted cornea was examined with stereographic microscope as well as transmission microscope (Olympus, Japan) equipped with Nomarski Interference Contrast (NIC) prism to enhance contrast between regions of the cornea that may have different refractive index. Imaging was later repeated on fresh corneas.

Measurements of Photoionization

Treatment of transparent biological media by femtosecond lasers can be achieved at least due to nonlinear nature of laser-matter interaction, which results in formation of quasi-free electrons via photoionization. Photoionization in transparent dielectrics can be achieved either via multiphoton ionization (MPI) or tunneling ionization. In the former, an electron absorbs several photons simultaneously, whereas the latter is characterized by the electromagnetic field that is strong enough to distort the Coulomb well so that the electron can escape the energy barrier.

Free electrons produced by MPI or tunneling ionization gain kinetic energy by absorbing photons in a process called 'inverse Bremsstrahlung'. The process includes collisions with heavy charged particles (ions or nuclei), which are needed for energy and momentum conservation. A sequence of inverse Bremsstrahlung events results in increase of the electron's kinetic energy that is now sufficient to produce another free electron via impact ionization. The sequence is repeated, resulting in growth of the free electron density in a process that resembles an avalanche.

Femtosecond laser-assisted treatment of ocular media can include photodisruption, which relies on formation of cavitation bubble(s) within the focal volume to create incision(s) in the interior of a cornea. Achieving an optical breakdown in the laser focus induces cavitation bubble.

It has been experimentally shown that this threshold in ocular and biological media is similar to the optical breakdown threshold in water. Since the number of free electrons produced during a single pulse is a function of irradiance, one could couple a femtosecond oscillator with a beam delivery system, which has an appropriate numerical aperture (NA) to confine density of the laser generated free electrons below the critical value needed for formation of dense plasma, as illustrated in FIGS. 18A and 18B.

FIG. 18A graphs the average lasing energy vs treatment lasing irradiance level curves. The optical breakdown is approximately $1.0 \times 10^{13}$ W cm−2 and the corresponding average energy intensity for the applied laser would be 0.319 W while the treatment applied an average energy 1.1525 nJ and the corresponding irradiance level is around $0.19 \times 10^{13}$ W cm$^{-2}$.

FIG. 18B graphs the objective numerical aperture vs treatment lasing irradiance level curve. The optical breakdown is approximately $1.0 \times 10^{13}$ W cm$^{-2}$ and numerical aperture required to achieve optical breakdown at treatment irradiance is 1.384.

In such a scenario, low-density plasma is formed, and treatment is reduced to ionization and dissociation of the water content within the focal volume. This treatment results in production of reactive oxygen species. Initially, ionization of the water molecule occurs, and the ejected electron is quickly hydrated resulting in formation of a solvated electron. Further, the cation radical of water, $H_2O+$, is rather unstable and react with a water molecule producing hydrogen ion $H_3O^+$, and hydroxyl radical $OH^*$. Concurrently dissociation of the excited water molecule occurs $H_2O^* \rightarrow H+ OH^*$.

These are the primary reactions which occur within $\sim 10^{-13}$ seconds, and are followed by secondary reactions in which H, $O_2^-$, $OH^-$, $H_2$, $H_2O_2$, $HO_2$ and other species, including singlet oxygen, are formed. In this study we have shown that similar effects are achieved when femtosecond oscillator is employed. Since the energy of a photon at 1059 nm wavelength is 1.17 eV, six photons are required to interact simultaneously with a bound electron to overcome the band gap of 6.5 eV, and produce electron-hole pair. The two-photon ionization is substituted with MPI, however, the nature of the chemical reactions and the radicals produces are likely the same.

FIG. 19 depicts results obtained via electron paramagnetic resonance (EPR) spectroscopy. FIG. 19A shows the results for femtosecond laser treated DMPO solution, while FIG. 19B illustrates a control sample. Due to short halflife of reactive oxygen species, spin-trapping was employed. Spin-trap reagent 5,5-dimethy-1-pyrroline-N-oxide (DMPO) solved in Dulbecco's phosphate-buffered saline (DPBS) has trapped OH* and $O_2^-$, created after the solution was ionized with femtosecond oscillator. The radicals of interest (hydroxyl radicals and superoxide anion radicals) are identified through an adduct, which is a product of their reaction with DMPO.

Measurements of Temperature Distribution and Refractive Index

Formation of radicals enables treatment of ocular tissue through their reaction with amino acids present in collagen fibrils. However, laser energy driven creation and subsequent acceleration of the free electrons also increases their kinetic energy, which is transferred to the surrounding particles via collisions and non-radiative recombination. The process results in the heating of the plasma within the focal volume. The energy density deposited into the focal volume is therefore product of the total number of free electrons produced by the pulse and the mean energy gain of each electron. Latter can be described as the sum of ionization potential and average kinetic energy. It is assumed that the focal volume has the shape of Gaussian ellipsoid, and thus, the spatial distribution of the energy density within the focal volume follows Gaussian distribution.

Significant rise of temperature within the focal volume and its immediate vicinity could have adverse effects. The one effect would be related to generation of a thermoelastic tensile stress wave, which is a function of the temperature distribution within the focal volume as well as the shape of the focal volume. Temperature rise due to the laser treatment could enable formation of a compressive stress wave, which propagates though the surrounding tissue. Thermal expansion is followed by tensile stress wave, governed by inertial forces, which travels in the opposite direction. If the amplitude of the tensile stress exceeds the tensile strength of the target material, a transient cavitation bubble will be formed regardless the fact that the optical breakdown has not been reached. The cavitation bubble could disrupt the collagen fibril arrangement resulting in localized change of refractive index ('corneal haze').

Figure 20:
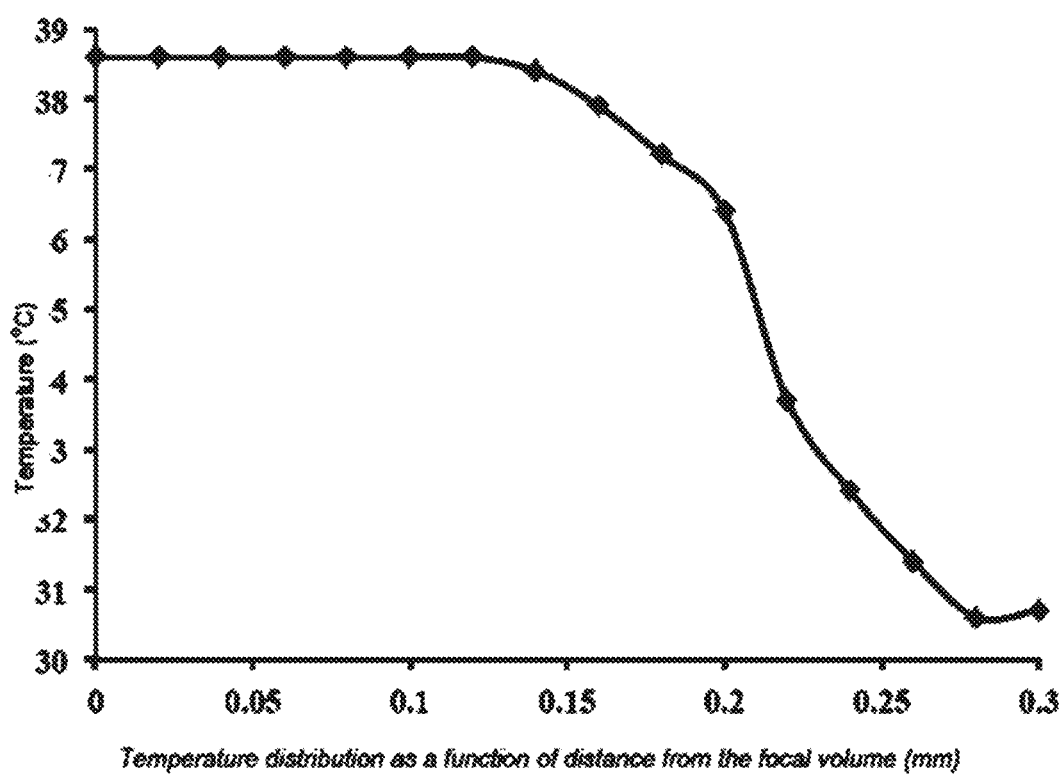
FIG. 20 illustrates a temperature distribution as a function of distance from the focal volume of an embodiment.

Another effect would be denaturation of collagen at elevated temperatures. Collagen denaturation transition occurs at 58° C. and the main denaturation transition occurs at 65° C. FIG. 20 illustrates a temperature distribution as a function of distance from the focal volume of an embodiment. Temperature measurements illustrated in FIG. 20 show that the maximum temperature increase is about 8° C., which remains constant within about 120 μm radius from the focal volume, after which it decreases sharply. As typical temperature of a human eye is around 35° C., the corneal treatment is very unlikely to cause any collagen denaturation.

Figure 21:
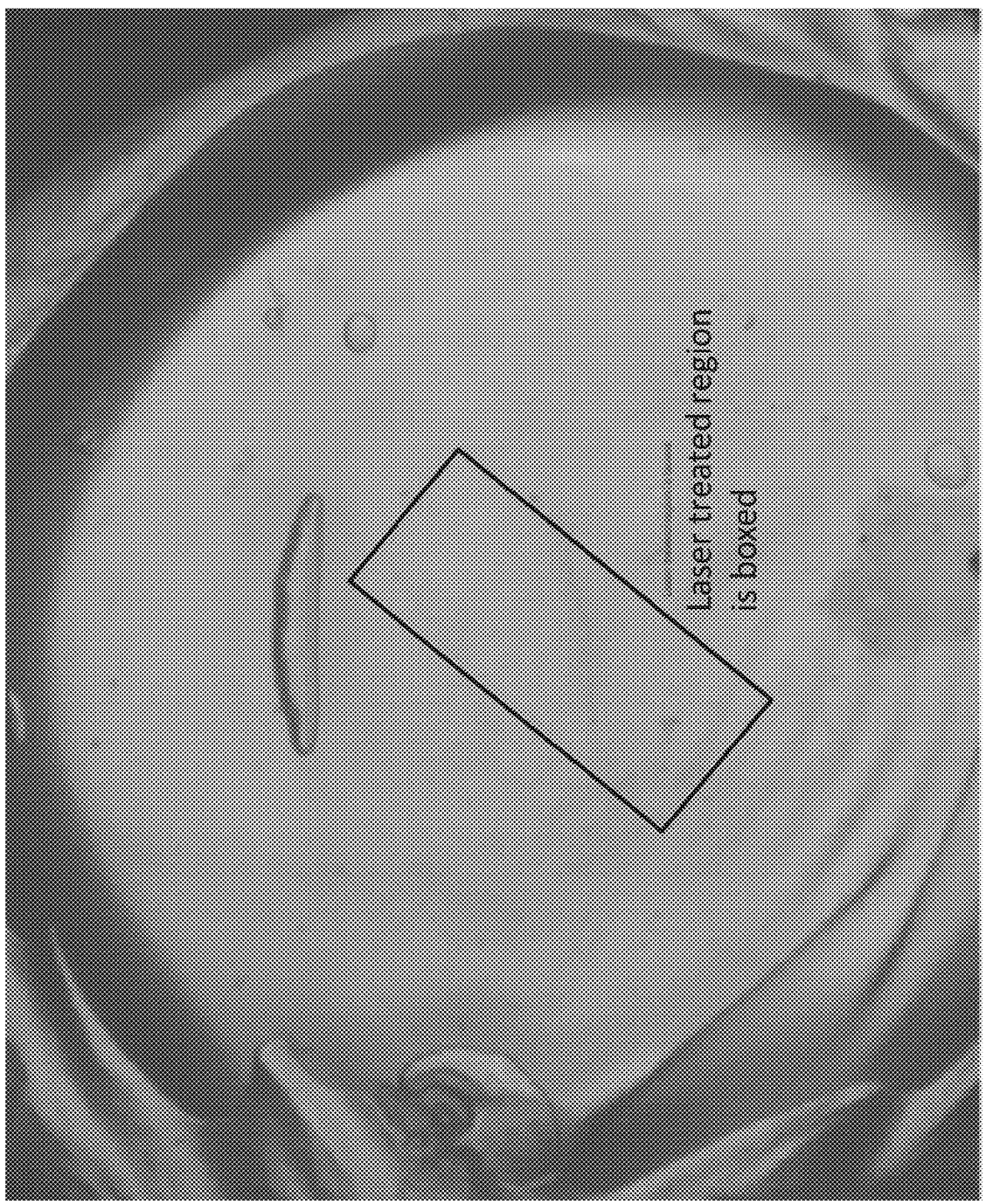
FIG. 21 illustrates a stereographic micrograph of a porcine cornea that has been treated according to an embodiment.

Corneas were also treated to investigate whether change in refractive index would occur as a consequence of disruption of collagen fibrils. Post-treatment images are illustrated in FIG. 21 and show no difference in the refractive index between treated region and the surrounding corneal tissue. Boxed region in the center has been treated with femtosecond laser following protocol above. Both stereographic and Normaski contrast micrographs show no difference in refractive index between treated and surrounding tissue.

The method and apparatus for cross-linking in cornea is applicable to other tissues, such as cartilage. As demonstrated through experiments described below, cross-linking was induced in cartilage. Inducing cross-linking in cartilage through femtosecond laser irradiation can be used to treat osteoarthritis, especially early osteoarthritis. Osteoarthritis (OA) is a severe degenerative disease with limited treatment options. Adult cartilage is an avascular connective tissue with an extracellular matrix (ECM) consisting of collagens (COL) and proteoglycans (PGs), with the former providing tensile strength and the latter being responsible for the compressive stiffness. Disruption of the COL network compromises the ability of cartilage to resist the swelling pressure of PGs, resulting in increased water content, decreased compressive stiffness, and greater vulnerability to progressive cartilage degeneration and loss of function. The onset of OA is characterized by changes in the structure of the collagen network, but not necessarily its content. Crosslinks stabilize the COL fiber network, and their disruption leads to loss of tensile strength and structural integrity of the bulk tissue. Targeted cross-linking of COL matrix is a pathway for cartilage repair and an impediment of OA progression.

The disclosed methods, devices, and systems for treatment of OA realized by the induction of crosslinks (CxLs) in the COL fiber network via optical interaction, for example, femtosecond laser irradiation. As explained above, the cross-linking can be induced by direct absorption of the radiated energy by the cartilage, or by inducing ionization in the aqueous medium in and around the cartilage. Newly induced CxLs may stabilize the COL network and therefore enhance the mechanical properties of OA-afflicted cartilage.

Experiments have successfully demonstrated that a femtosecond oscillator operating in low-density plasma regime is capable of enhancing the mechanical properties of corneal tissue, which predominantly consists of type I COL, as well as articular cartilage.

The following experiments were used to validate the treatment of cartilage with femtosecond laser irradiation for inducing cross-linking. Cartilage explants 5 mm round by 1.6 mm and 3.0 mm thickness were obtained using a 3D printed slicer. The cartilage pieces were harvested from three immature bovine proximal tibias with their articular surfaces intact. The treatment was performed with a Nd:Glass High-Q Femtosecond laser oscillator system (temporal pulse width of 99 fs and 52.06 MHz repetition rate) coupled with a 3-axis translational stage (Thorlabs, Inc.). The output wavelength was centered around 1060 nm, and the high numerical aperture objective (Zeiss, Plan Neofluar 40×/0.6) delivered about 60 mW at the focal point. The treatment consisted of applying laser pulses by moving the stage in a x-y plane such that the laser path followed a zigzag pattern at a feed rate of 2.2 mm/s, thus treating a planar surface at the specific depth. The treatment was repeated at different depths, effectively inducing 'treatment layers'. However, in embodiments the laser treatment can be applied through an optical guide to deliver the light to a patient. In an exemplary embodiment, the laser treatment is provided through an endoscope.

In the experiments, multiple treatment layers parallel to the superficial surface were applied with 50 μm distance between two consecutive planes. The specimens were gently inserted in a custom made holder with 5 mm holes and kept moisturized during the treatment in a PBS bath. Two batches of experiments were carried out in this study, with each batch executed on a different joint. In the first batch, six specimens were treated with the femtosecond laser, each requiring 1 hour, and was paired with an untreated control specimen that was placed next to the treated sample in the identical holder. All conditions except the laser treatment were the same for the paired controls and treated samples during the test. Two additional samples were used as fresh controls. In the second batch, five controls and five treated samples were used. Three of the treated samples received five laser treated layers. The remaining two specimens were exposed to ten laser treated layers. Cartilage explants were tested in a custom device under unconfined compression, using a creep tare load (0.1 N, 400 s) followed by stress-relaxation to 10% strain (0.5 µm/s ramp, 1800 s). The equilibrium Young's modulus (Ey) was calculated from the explant cross-sectional area, the equilibrium load and the displacement. One-way ANOVA analysis was performed to analyze data.

The results of the experiments confirm the formation of cross-links in the cartilage. In the first batch of experiments, laser treated samples were stiffened about 21% in comparison to the controls (p<0.003). Both paired and fresh controls had similar Young's modulus (FIG. 1a). The second batch of experiments has shown similar stiffening of the specimens treated with five layers in comparison to the controls (p<0.05). However, the samples treated with ten layers showed a significant decrease in Ey (p<0.001, FIG. 1b).

Collagen (COL) is the major structural protein of most connective tissues. The structural integrity and mechanical properties of articular cartilage are significantly affected by collagen cross-links, chemical compounds that connect COL fibrils as well as molecules within the collagen. When a femtosecond oscillator operates in a regime below the optical breakdown threshold, a low density plasma is created within the focal volume. This plasma is not sufficiently energetic to produce a shock wave, and thus the interaction between the laser and the affected tissue is photochemical, which leads to ionization of the matter within the focal volume and in its vicinity. Radicals produced by the ionization field interact with the COL fibrils, which in turn produce CxLs. Therefore, laser induced CxLs are responsible for stiffening of the cartilage, which in turn yields enhancement of mechanical properties illustrated in FIGS. 22A and 22B.

Free radicals (or reactive oxygen species) created by the multiphoton ionization are responsible for COL CxLs within articular cartilage. The experiments confirm that ultrafast irradiation with infrared (IR) laser pulses ionize water molecules in the target tissue. The recognition that cross-linking can be achieved by ionizing water molecules, rather than ionizing the target tissue directly, enables the use of lasers at wavelengths that do not directly form covalent bonds in the collagen. Thus, wavelengths are selected to ionize water molecules and generate reactive oxygen species. The reactive oxygen species in turn induce cross-linking in the collagen of the treated cartilage. In an embodiment, the interaction mechanism is multiphoton, rather than two-photon ionization. This allows treatment with IR, and other wavelengths, rather than ultraviolet (UV) pulses and much lower pulse energies. Ionization of the water content within the focal volume in the interior of the articular cartilage yields hydroxyl radicals, OH* and hydrogen ions $H_3O+$. Singlet oxygen may also be produced among other species. Free radicals interact with the COL matrix producing cross-links.

These newly formed cross-links can be different from the ones that naturally occur in ECM, such as hydroxylysylpyridinoline. For example, one of the CxLs formed can be 1,3-dityrosine.

The disclosed study introduces a novel treatment of early OA and determines effectiveness of femtosecond laser treatment in delaying the progression of collagen fatigue failure using a well-characterized in vitro damage model of mechanically induced OA in both vital and devitalized articular cartilage.

Figures 22A, 22B:
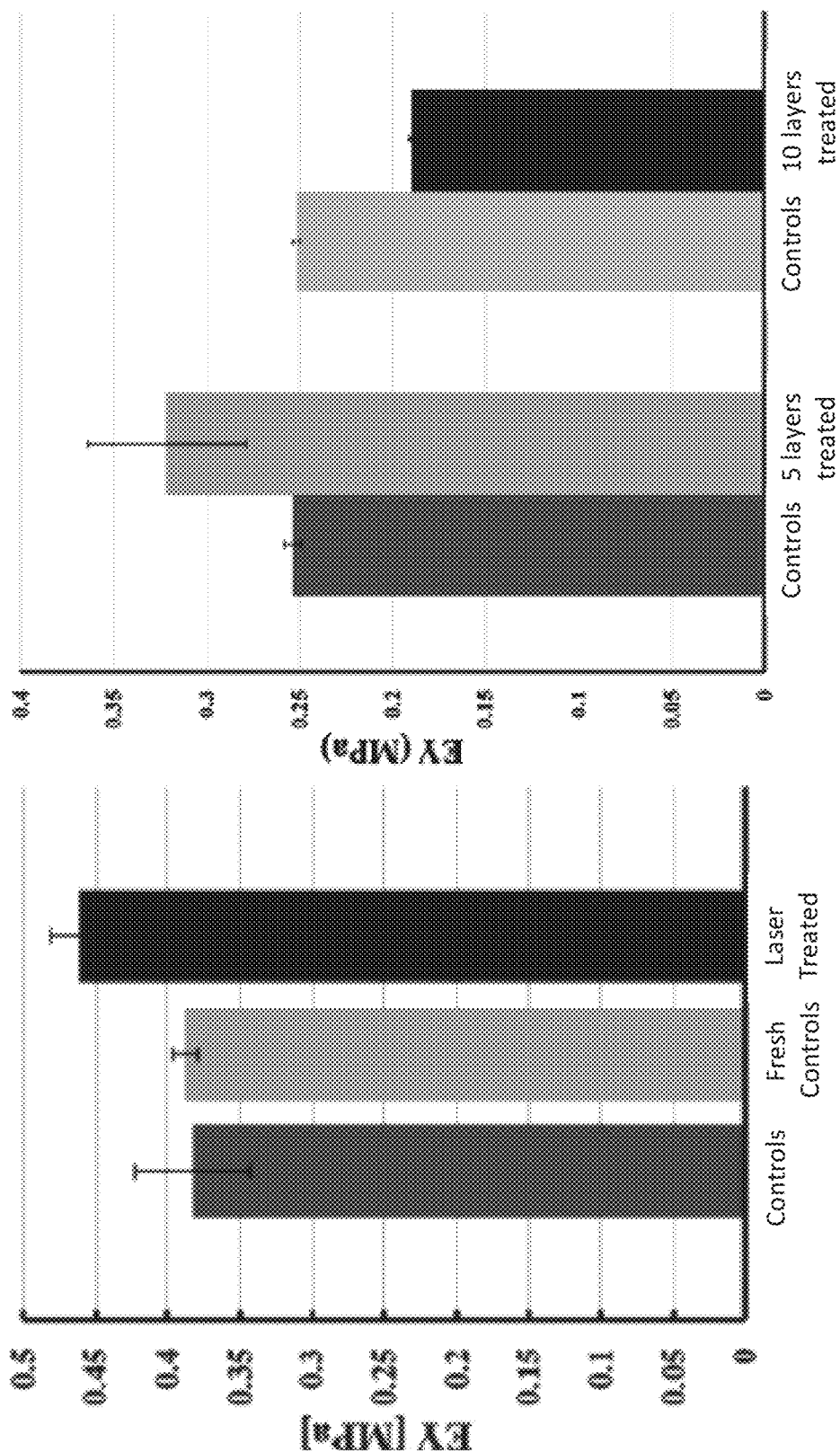
FIGS. 22A-22B show results of treatment of cartilage.

FIG. 22A shows results of mechanical property characterization of laser treated samples, paired controls and fresh controls. FIG. 22B shows results of mechanical property test of controls, five layers treated samples and ten layers treated samples. (*p<0.05: statistical change from corresponding initial value.)

In an exemplary embodiment of the disclosed subject matter, a method of inducing cross-linking in a tissue containing water includes generating reactive oxygen species by ionizing water molecules, the ionizing including focusing light on a tissue containing water. In the exemplary embodiment, the focusing and intensity of the light is sufficient to cause ionization of water without causing optical breakdown of molecules of the tissue. In the exemplary embodiment, the range of frequencies of the light is selected to excite water molecules without directly forming covalent bonds.

In an exemplary embodiment of the disclosed subject matter, a method of inducing cross-linking in a tissue containing water includes generating reactive oxygen species from water molecules, the generating including focusing infrared light on a tissue containing water. In the exemplary embodiment, the focusing and intensity of the infrared light is sufficient to cause ionization of water without causing optical breakdown of molecules of the tissue and the range of frequencies of the infrared light are selected to excite water molecules such that cross-linking of collagen is caused by the reactive oxygen species rather than by the formation of covalent bonds.

In an exemplary embodiment of the disclosed subject matter, a method of inducing cross-linking in a tissue containing water includes forming cross-links locally in collagen in the tissue by means of reactive oxygen species by generating reactive oxygen species from water molecules, the generating including focusing infrared light on a tissue containing water at an intensity and range of frequencies effective to ionize water without the formation of covalent bonds and without inducing optical breakdown.

In an exemplary embodiment of the disclosed subject matter, a system for reshaping curvature of a region of a cornea having an initial curvature includes illumination optics configured to project an illumination pattern onto at least a portion of the cornea. In the exemplary embodiment, a camera is configured to record a pattern reflection from the at least a portion of the cornea and a control system, coupled to the camera, is configured to convert the pattern reflection to a corneal topography, and to compare the corneal topography to a desired corneal topography to determine a deformation map. In the exemplary embodiment, a laser system is configured to induce ionization in the region of the cornea according to the deformation map to reshape the region from the initial curvature to a new curvature. In the exemplary embodiment, a coupling device may be configured to stabilize the laser system with respect to the cornea.

In an exemplary embodiment of the disclosed subject matter, an apparatus for adapting a laser system for reshaping curvature of a region of a cornea having an initial curvature includes a control system, adapted to be coupled to the laser system and configured to compare an existing corneal topography of at least a portion of the cornea to a desired corneal topography to determine a deformation map. In the exemplary embodiment, laser modification optics are coupled to the control system and configured to adjust laser output of the laser system, to modify a region of the cornea according to the deformation map.

In an exemplary embodiment of the disclosed subject matter, a method of reshaping curvature of a region of a cornea having an initial curvature includes inducing partial ionization in a region of the cornea by applying laser light energy below optical breakdown.

In an exemplary embodiment of the disclosed subject matter, a method of inducing cross-linking in tissue includes inducing ionization in a region of the tissue by applying laser light energy below the optical breakdown level at wavelengths effective to generated reactive oxygen species in water without forming covalent bonds in collagen.

In an exemplary embodiment of the disclosed subject matter, a system for reshaping curvature of a region of a cornea having an initial curvature includes illumination optics configured to project an illumination pattern onto at least a portion of the cornea, a camera configured to record a pattern reflection from the at least a portion of the cornea, and a control system, coupled to the camera, configured to convert the pattern reflection to a corneal topography, and to compare the corneal topography to a desired corneal topography to determine a deformation map. In the exemplary embodiment, a laser system is configured to induce ionization in the region of the cornea according to the deformation map to reshape the region from the initial curvature to a new curvature, a coupling device is configured to stabilize the laser system with respect to the cornea, and the laser system generates a range of frequencies of light selected to excite water molecules such that cross-linking of collagen is caused by the reactive oxygen species generated thereby without directly forming covalent bonds. In the exemplary embodiment, the laser system has focusing optics that generate a maximum intensity that is lower than a level that would produce optical breakdown in the human cornea.

In an exemplary embodiment of the disclosed subject matter, an apparatus for adapting a laser system for reshaping curvature of a region of a cornea having an initial curvature includes a control system, adapted to be coupled to the laser system and configured to compare an existing corneal topography of at least a portion of the cornea to a desired corneal topography to determine a deformation map. In the exemplary embodiment, laser modification optics are coupled to the control system and configured to adjust laser output of the laser system, to modify a region of the cornea according to the deformation map. In the exemplary embodiment, the laser modification optics generate light of a predefined frequency range and include focusing optics sufficient to produce intensity of laser light below the optical breakdown level sufficient to ionize water without generating covalent bonds in collagen.

In an exemplary embodiment of the disclosed subject matter, a method of changing the mechanical properties of tissues containing collagen, includes focusing light on living tissue to generate reactive oxygen species from water in a tissue without directly generating covalent bonds in collagen in the tissue.

In an exemplary embodiment of the disclosed subject matter, a method of treating tissue includes irradiating aqueous media in or surrounding the tissue with a laser at an energy level that avoids breakdown in the tissue until reactive oxygen species are produced, and inducing cross-linking in tissue with the produced reactive oxygen media.

In an exemplary embodiment of the disclosed subject matter, a system for treating cartilage, the system includes a laser system, configured to induce ionization in a region of the cartilage according to a treatment pattern, the laser system generating a range of frequencies of light selected to excite water molecules such that cross-linking of collagen is caused by the reactive oxygen species generated thereby without directly forming covalent bonds, the laser system having focusing optics that generate a maximum intensity that is lower than a level that would produce optical breakdown in the human cornea.

In an exemplary embodiment of the disclosed subject matter, a method of reshaping a patient's cornea from a first shape to a second shape, includes irradiating the cornea with a laser light in the absence of a photosensitizer in or on the cornea, the laser light having energy sufficient to cause ionization of water without causing optical breakdown of molecules of the tissue. In the exemplary embodiment, the method also includes generating reactive oxygen species by ionizing water molecules in or on the cornea, and inducing cross-linking in the cornea by the generated reactive oxygen species, wherein the induced cross-linking changes the shape of the cornea from the first shape to the second shape.

According to any of the foregoing exemplary embodiments of the disclosed subject matter, the measuring of the topography further includes projecting an illumination pattern on the cornea, recording a pattern reflection from the cornea with a camera, and converting the pattern reflection into the topography of the cornea.

According to any of the foregoing exemplary embodiments of the disclosed subject matter, the tissue is a cornea, and the focusing includes projecting an illumination pattern on the cornea.

According to any of the foregoing exemplary embodiments of the disclosed subject matter, the focusing includes scanning a laser over a region of a cornea to be modified.

According to any of the foregoing exemplary embodiments of the disclosed subject matter, the scanning includes scanning a femtosecond laser.

According to any of the foregoing exemplary embodiments of the disclosed subject matter, the scanning includes scanning a femtosecond laser having an average power output from about 10 mW to about 100 mW.

According to any of the foregoing exemplary embodiments of the disclosed subject matter, the scanning includes scanning a femtosecond laser having a pulse energy of from about 0.1 nJ to about 10 nJ.

According to any of the foregoing exemplary embodiments of the disclosed subject matter, the scanning includes scanning in a pattern of exposure comprising a circle, annulus, and/or ellipse.

According to any of the foregoing exemplary embodiments of the disclosed subject matter, the scanning includes scanning in multiple layers of the cornea.

According to any of the foregoing exemplary embodiments of the disclosed subject matter, the focusing includes projecting an illumination pattern on the cornea.

According to any of the foregoing exemplary embodiments of the disclosed subject matter the focusing includes scanning a laser over a region of a cornea to be modified.

According to any of the foregoing exemplary embodiments of the disclosed subject matter the scanning includes scanning a femtosecond laser.

According to any of the foregoing exemplary embodiments of the disclosed subject matter, the laser system is configured to cross-link collagen in the cornea according to the deformation map.

According to any of the foregoing exemplary embodiments of the disclosed subject matter, the laser system comprises a femtosecond laser.

According to any of the foregoing exemplary embodiments of the disclosed subject matter, the femtosecond laser comprises a Nd:Glass femtosecond laser.

According to any of the foregoing exemplary embodiments of the disclosed subject matter, the femtosecond laser comprises a laser having a pulse width of from about 50 fs to 150 fs.

According to any of the foregoing exemplary embodiments of the disclosed subject matter, the femtosecond laser comprises a laser having an average power from about 10 mW to about 100 mW.

According to any of the foregoing exemplary embodiments of the disclosed subject matter, the femtosecond laser comprises a laser adapted to emit light in the wavelength range from about 600 nm to about 1600 nm.

According to any of the foregoing exemplary embodiments of the disclosed subject matter, the femtosecond laser comprises a laser adapted to emit light in the infrared frequency range.

According to any of the foregoing exemplary embodiments of the disclosed subject matter, the laser system comprises a high magnification objective lens and a galvanometer configured to raster a laser beam.

According to any of the foregoing exemplary embodiments of the disclosed subject matter, the laser system further comprises an attenuator.

According to any of the foregoing exemplary embodiments of the disclosed subject matter, the laser modification optics are configured to cross-link collagen in the region of the cornea according to the deformation map.

According to any of the foregoing exemplary embodiments of the disclosed subject matter, the laser modification optics further comprise an attenuator to reduce laser output power.

According to any of the foregoing exemplary embodiments of the disclosed subject matter, the illumination pattern comprises a pattern generated by a continuous wave laser.

According to any of the foregoing exemplary embodiments of the disclosed subject matter, the new curvature corresponds with the desired topography.

According to any of the foregoing exemplary embodiments of the disclosed subject matter, the region of the cornea to be modified is based at least in part on a deformation map.

According to any of the foregoing exemplary embodiments of the disclosed subject matter, the inducing partial ionization comprises scanning a laser over the region of the cornea to be modified.

According to any of the foregoing exemplary embodiments of the disclosed subject matter, the scanning comprises scanning a femtosecond laser having an average power output from about 10 mW to about 100 mW.

According to any of the foregoing exemplary embodiments of the disclosed subject matter, the femtosecond laser has a pulse energy of from about 0.1 nJ to about 10 nJ.

According to any of the foregoing exemplary embodiments of the disclosed subject matter, the majority of the laser power is in wavelengths, or integral fractions thereof, that are not absorbed directly by amino acids in the collagen.

According to any of the foregoing exemplary embodiments of the disclosed subject matter, the majority of the laser power is in wavelengths, or integral fractions thereof, that are absorbed directly by water to form reactive oxygen species.

According to any of the foregoing exemplary embodiments of the disclosed subject matter, the tissue is cartilage, and the applying the laser light includes projecting an illumination pattern on the cartilage.

According to any of the foregoing exemplary embodiments of the disclosed subject matter, the inducing ionization comprises scanning a laser over a region of cartilage to be modified and the inducing is effective to generate reactive oxygen species as a result of multiphoton interaction with water.

According to any of the foregoing exemplary embodiments of the disclosed subject matter, the laser light has a wavelength in the infrared region of the spectrum.

According to any of the foregoing exemplary embodiments of the disclosed subject matter, the laser has a range of wavelengths with most of the power at wavelengths that are not directly absorbed by collagen or integral multiples thereof.

According to any of the foregoing exemplary embodiments of the disclosed subject matter, the scanning comprises scanning a pulsed laser.

According to any of the foregoing exemplary embodiments of the disclosed subject matter, the laser is irradiated on the tissue in the absence of a photosensitizer.

According to any of the foregoing exemplary embodiments of the disclosed subject matter, the femtosecond laser includes a laser adapted to emit light in the wavelength range from about 600 nm to about 1100 nm.

According to any of the foregoing exemplary embodiments of the disclosed subject matter, the laser system includes a high magnification objective lens and a galvanometer configured to raster a laser beam.

According to any of the foregoing exemplary embodiments of the disclosed subject matter, measuring of the topography further includes projecting an illumination pattern on the cornea, recording a pattern reflection from the cornea with a camera, and converting the pattern reflection into the topography of the cornea.

According to any of the foregoing exemplary embodiments of the disclosed subject matter, the illumination pattern includes a pattern generated by a continuous wave laser.

According to any of the foregoing exemplary embodiments of the disclosed subject matter, the new curvature corresponds with the desired topography.

According to any of the foregoing exemplary embodiments of the disclosed subject matter, the tissue being treated by the laser lacks a photosensitizer.

According to any of the foregoing exemplary embodiments of the disclosed subject matter, the irradiating includes inducing low-density plasma in the tissue and thereby ionizing one or more water molecules in the aqueous media such that at least an electron is ejected from the one or more ionized water molecules.

According to any of the foregoing exemplary embodiments of the disclosed subject matter, the irradiating includes outputting pulses of the laser with a duration of each pulse shorter than 1000 femtoseconds.

According to any of the foregoing exemplary embodiments of the disclosed subject matter, the system includes an optical pathway for guiding the laser light emitted from the femtosecond laser to the cartilage.

According to any of the foregoing exemplary embodiments of the disclosed subject matter, the optical pathway includes an endoscope.

According to any of the foregoing exemplary embodiments of the disclosed subject matter, the second shape has a steeper curvature than the first shape.

According to any of the foregoing exemplary embodiments of the disclosed subject matter, the second shape has a less steep curvature than the first shape.

It has, thus, been shown that femtosecond oscillator can ionize target material under loose conditions, which enables applications in transparent dielectrics on a micro-scale. When operating below optical breakdown threshold, femtosecond laser produces low-density plasma, and thus generates reactive oxygen species (also referred to as free radicals herein) within the focal volume. Newly formed radicals quickly react with the surrounding media and alter its chemical composition. When the surrounding media includes collagen fibers, collagen cross-linking occurs. Such treatment regime is suitable for treatment organic transparent dielectrics such as corneal tissue. Radicals react with amino acids in the collagen triple helix to form crosslinks, which enhances mechanical properties of corneal stroma.

The description herein merely illustrates the principles of the disclosed subject matter. Various modification and alterations to the described embodiments will be apparent to those skilled in the art in view of the teachings herein. Accordingly, the disclosure herein is intended to be illustrative, but not limiting, of the scope of the disclosed subject matter.

The invention claimed is:

1. A method of inducing cross-linking in a cartilage, the method comprising:
   generating reactive oxygen species from water molecules present in the cartilage by ionizing the water molecules within the cartilage, without a photosensitizer present in or on the cartilage, with a focused light at infrared frequencies irradiated on the cartilage, wherein
   the focused light at infrared frequencies is emitted by a femtosecond laser having an average power output from 10 mW to 100 mW, a pulse energy from 0.1 nJ to 10 nJ and a pulse width from 50 to 150 femtoseconds,
   focusing and intensity of the focused light at the infrared frequencies causes ionization of water without causing optical breakdown of molecules of the cartilage, and
   the focused light at the infrared frequencies includes a range of frequencies that excite the water molecules without directly forming covalent bonds in collagen.

2. The method of claim 1, wherein
   the focused light at the infrared frequencies projects an illumination pattern on the cartilage.

3. The method of claim 1, wherein the focused light at the infrared frequencies scans the femtosecond laser over a region of the cartilage to be treated.

4. The method according to claim 1, further comprising:
   splitting a beam of the femtosecond laser to multiple scanning objectives, wherein
   the focused light is emitted by a laser head with the multiple scanning objectives.

5. A method of inducing cross-linking in cartilage, comprising:
   inducing ionization in a region of the cartilage by applying laser light energy below an optical breakdown level at wavelengths effective to generated reactive oxygen species in water contained within the cartilage without directly forming covalent bonds in collagen.

6. The method of claim 5, wherein:
   the inducing ionization comprises scanning a laser over a region of cartilage to be treated; and
   the inducing is effective to generate reactive oxygen species as a result of multiphoton interaction with water.

7. The method of claim 6, wherein the laser light has a wavelength in an infrared region of the spectrum.

8. The method of claim 6, wherein the laser has a range of wavelengths with most of its power at wavelengths that are not directly absorbed by collagen or integral multiples thereof.

9. The method of claim 6, wherein the scanning comprises scanning a femtosecond laser having an average power output from about 10 to about 100 mW.

10. The method of claim 6, wherein the scanning comprises scanning a femtosecond laser having a pulse energy of from about 0.1 nJ to about 10 nJ.

11. A system for treating cartilage, the system comprising:
    a laser system, configured to induce ionization in a region of the cartilage according to a treatment pattern, the laser system generating a range of frequencies of light selected to excite water molecules such that cross-linking of collagen is caused by reactive oxygen species generated by the light without directly forming covalent bonds in collagen contained in the cartilage, the laser system having focusing optics that generate a maximum intensity that is lower than a level that would produce optical breakdown in the cartilage.

12. The system of claim 11, wherein the laser system comprises a femtosecond laser.

13. The system of claim 12, wherein the femtosecond laser comprises a Nd:Glass femtosecond laser.

14. The system of claim 13, wherein the femtosecond laser comprises a laser having a pulse width of from about 50 to 150 fs.

15. The system of claim 13, wherein the femtosecond laser comprises a laser having an average power from about 11 to about 100 mW.

16. The system of claim 13, wherein the femtosecond laser comprises a laser adapted to emit light in a wavelength range from about 600 nm to about 1100 nm.

17. The system of claim 13, wherein the femtosecond laser comprises a laser adapted to emit light in an infrared frequency range.

18. The system of claim 13, further comprising an optical pathway for guiding the laser light emitted from the femtosecond laser to the cartilage.

19. The system of claim 18, wherein the optical pathway includes an endoscope.

20. The system of claim 11, wherein the laser system further comprises an attenuator.

* * * * *